US007851461B2

(12) United States Patent
Raskov

(10) Patent No.: US 7,851,461 B2
(45) Date of Patent: *Dec. 14, 2010

(54) COMBINATION DOSAGE OF A CYCLOOXYGENASE (COX) INHIBITOR, A VITAMIN $D_3$ INCLUDING ANALOGUES AND METABOLITES THEREOF AND/OR CALCIUM FOR PREVENTION OF EPITHELIAL CANCER

(75) Inventor: Hans Henrik Raskov, Frederiksberg (DK)

(73) Assignee: Colotech A/S, Copenhagen K (DK)

( * ) Notice: Subject to any disclaimer, the term of this patent is extended or adjusted under 35 U.S.C. 154(b) by 148 days.

This patent is subject to a terminal disclaimer.

(21) Appl. No.: 10/474,058

(22) PCT Filed: Apr. 5, 2002

(86) PCT No.: PCT/DK02/00231

§ 371 (c)(1),
(2), (4) Date: Oct. 6, 2003

(87) PCT Pub. No.: WO02/080889

PCT Pub. Date: Oct. 17, 2002

(65) Prior Publication Data

US 2004/0116393 A1 Jun. 17, 2004

Related U.S. Application Data

(63) Continuation-in-part of application No. 09/825,891, filed on Apr. 5, 2001, now Pat. No. 6,703,380, which is a continuation-in-part of application No. PCT/DK00/00546, filed on Sep. 29, 2000.

(30) Foreign Application Priority Data

Sep. 29, 1999 (DK) ................................ 1999 01390

(51) Int. Cl.
*A61K 31/60* (2006.01)
(52) U.S. Cl. ...................................... 514/165; 514/167
(58) Field of Classification Search ................. 514/165, 514/167
See application file for complete search history.

(56) References Cited

U.S. PATENT DOCUMENTS

| 5,770,215 A | 6/1998 | Moshyedi .................... 424/440 |
| 5,948,443 A | 9/1999 | Riley et al. .................. 424/643 |

FOREIGN PATENT DOCUMENTS

| DE | 43 34 154 | 4/1995 |
| EP | 0 205 025 | 12/1986 |
| EP | 0 412 110 | 7/1993 |
| GB | WO 96/41645 | 12/1996 |
| WO | WO 89/10351 | 11/1989 |
| WO | WO 93/09093 | 5/1993 |
| WO | WO 93/19044 | 9/1993 |
| WO | WO 94/14766 | 7/1994 |
| WO | WO 94/26707 | 11/1994 |
| WO | WO 95/02577 | 1/1995 |
| WO | WO 95/03273 | 2/1995 |
| WO | 01/22974 A1 | 4/2001 |

OTHER PUBLICATIONS

Steele et al., Journal of Cellular Biochemistry, Supplement 20:32-54 (1994).*
Feskanich et al. British Journal of Cancer, 2007, vol. 97, pp. 1295-1299.*
Michaud et al. Am. J. Epidemiol., 2000, vol. 152, No. 12, pp. 1145-1153.*
Trujillo, M. A. et al., Dig. Dis. Sci. 39:2260-2266 (1994), "Non-steroidal antiinlfammatory agents in chemoprevention of colorectal cancer. At what cost?".
Caplan, L. S. et al., Curr. Opin. Oncol 8:441-446 (1996), "Secondary prevention of cancer".
Key, Jak et al., BMJ 313:775-779 (1996), "Dietary habits and mortality in 11000 vegetarians and health conscious people: results of a 17 year follow-up".
Garland, C. F. et al., Lancet 307-309 (1985), "Dietary vitamin D and calcium and risk of colorectal cancer: a 19-year prospective study in men".
Garland, C. F. et al., Lancet 18:1176-1178 (1989), "Serum 25 hydroxyvitamin D and colon cancer: eight-year prospective study".
Garland, C. F. et al., Am. J. Clin. Nutr. 54:193S-201S (1991), "Can colon cancer incidence and death rates be reduced with calcium and vitamin D?".
Kune, G. A. et al., "Colorectal cancer risk, chronic illnesses, operations and medications: case control results from the Melbourne Colorectal Cancer Study", (1988) Cancer Res. 48:4399-4404.
Suh, O. et al., Cancer 72:1171-1177 (1993), "Aspirin use, cancer and polyps of the large bowel".

(Continued)

*Primary Examiner*—James D Anderson
(74) *Attorney, Agent, or Firm*—Knobbe Martens Olson & Bear LLP

(57) ABSTRACT

The present invention relates to a method for prevention of epithelial cancer such as lung, bladder, prostate or gynaecological cancer or the initiation and/or progression of epithelial cancer such as lung, bladder, prostate or gynaecological cancer in a human comprising administering to the human of a combination dosage of a cyclooxygenase (COX) inhibitor, a vitamin $D_3$ including analogues and metabolites thereof and/or calcium. In a further aspect the invention relates to a method for reducing the effective dosage of ASA in a chemopreventive treatment of epithelial cancer in a human by co-administration with a non toxic dosage of a vitamin $D_3$ including analogues and metabolites thereof and/or Ca in the form of a combination dosage. In another embodiment the invention relates to the use of a cyclooxygenase (COX) inhibitor, a vitamin $D_3$ including analogues and metabolites thereof and/or calcium for the preparation of a medicament for the prevention of epithelial cancer such as lung, bladder, prostate or gynaecological cancer or the initiation and/or progression of epithelial cancer such as lung, bladder, prostate or gynaecological cancer.

22 Claims, 3 Drawing Sheets

OTHER PUBLICATIONS

Figure 1:
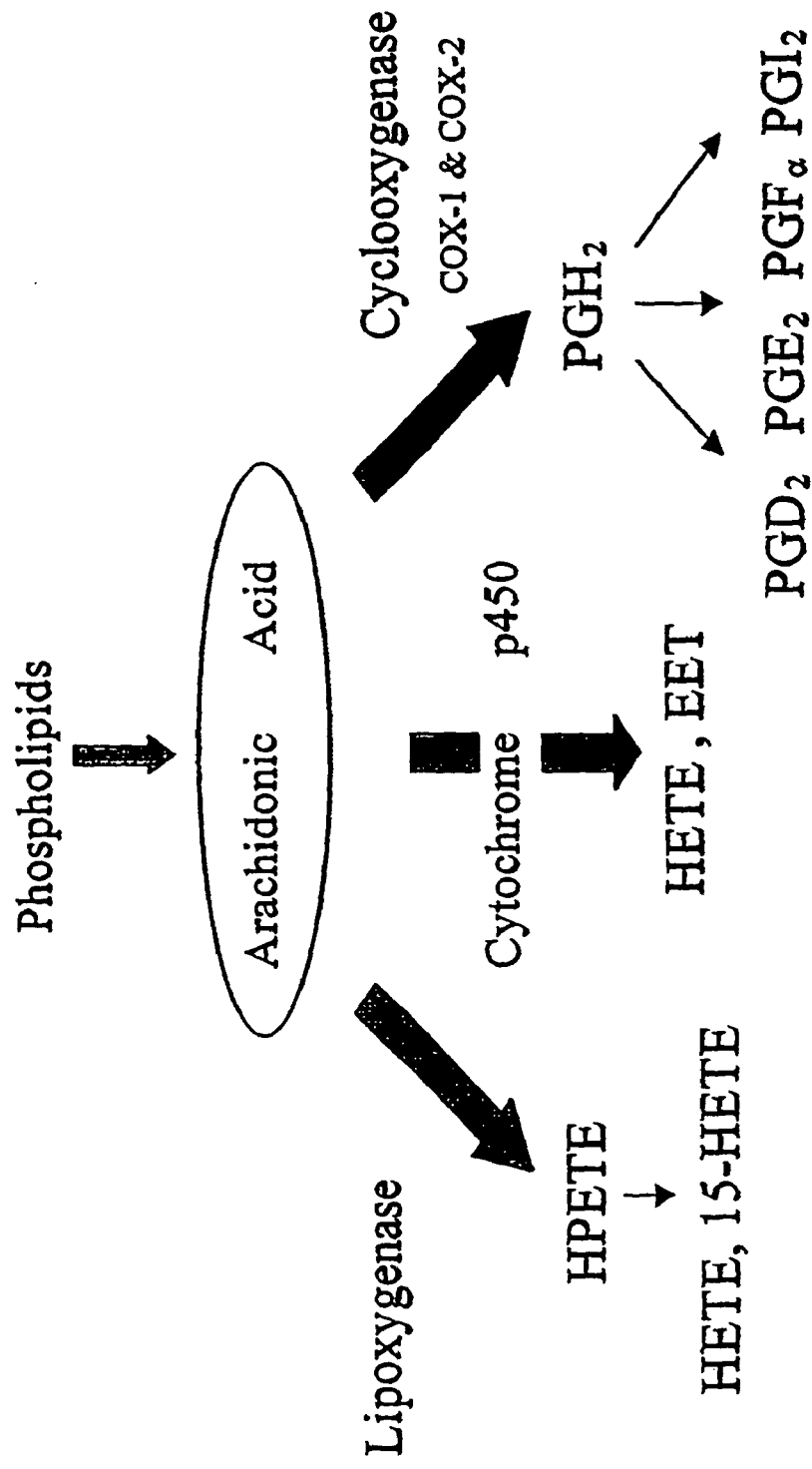

Thun, M. J. et al., "Aspirin use and reduced risk of fatal colon cancer", 1991 N. Engl. J. Med. 325:1593-1596.

Buring, J. E. et al., "Nonsteroidal antiinflammatory drugs and colorectal cancer", 1994 Cancer 74:1837-1839.

Heath, C. W. et al., "Nonsteroidal antiinflammatory and human cancer", 1994 Cancer 74:2885-2888.

Pence, BC., "Role of calcium in colon cancer prevention: experimental and clinical studies", 1993 Mut Res 290:87-95.

Duris, I. et al., "Calcium chemoprevention in colorectal cancer", 1996 Hepatogastro-enterol 43:152-154.

Buset, M. et al., "Inhibition of human colonic epithelial cell proliferation in vivo and in vitro by calcium" 1986 Cancer Res. 46:5426-5430.

Wargovich, M. J. et al., "Calcium and vitamin D modulate mouse colon epithelial proliferation and growth characteristics of a human colon tumor cell line", 1987 Can J. Physiol Pharmacol 65:472-477.

Dorudi, S. et al., "Levels of expression of E-cadherin m-RNA in colorectal cancer correlates with clinical outcome", 1995 Br. J. Cancer 71:614-616.

Newmark, H. L. et al., "Calcium, vitamin D and colon cancer", 1992 Cancer Research 52:20067S-2070S.

Rasmussen, H., "The calcium messenger system", 1986 N. Engl. J. Med 314:1094-1101.

Llor, X et al., "K-ras mutations in 1,2 dimethylhydrazine induced colonic tumors: effects of supplemental diatary calcium and vitamin D deficiency", 1991 Cancer Res. 51. 4305-4309.

Reshef, R. et al., "Effect of a calcium enriched diet on the colonic epithelial hyperproliferation induced by N-methyl-N-nitro-N-nitrosoguanidine in rats on a low calcium and fat diet", 1990 Cancer Res. 50:1764-1767.

Kane, K. F. et al., "Functional vitamin D3 receptors are present in human colorectal neoplasms", 1995 Gastroente-rology 108:A487.

Cross, H. S. et al., "Vitamin D receptor and cytokeratin expression may be expression indicators in human colon cancer", 1996 Anticancer Res. 16: 2333-2338.

Eisman, J. A. et al., "Suppression of in vivo growth of human cancer solid xenografts by 1,25-dihydroxyvitamin D3", 1987 Cancer Res. 47:21-25.

Ternent, C. et al., "Lipoxygenase blockade inhibits growth factor-induced colonic cancer cell proliferation", 1999 Abstract, ASCRS Ann. Meeting 1999.

Marcus, A. J., "Aspirin as prophylaxis against colorectal cancer", 1995 N. Engl. J. Med. 333:656-658.

Frolich, J. C., "A classification of NSAIDs according to the relative inhibition of cyclooxygenase enzymes", 1997 TIPS 18: 30-34.

Hanif, A. P. et al., "NSAIDs inhibit the growth of colon cancer cell lines by a prostaflandin independant pathway", 1995 Gastroenterology 108:A478.

Ahnen, D. et al., "Sulindac sulfide and sulfone both inhibit the growth of colon cancer cell lines by inducing apoptosis", 1995 Gastroenterology 108:A443.

Alberts, D. S. et al., "Do NSAIDs exert their colon cancer chemoprevention activities through the inhibition of mucosal prostaglandin synthetase?", 1995 J. Cell Biochem s22: 18-23.

Kahlenberg, M. et al., "Nonsteroidal antiinflammatory drugs (NSAID's) reduce genomic instability in colorectal tumor cells", 1998 Abstract. Surgical Oncology Societies 51st Annual Cancer Symposium 1998.

Levy, G., "Prostataglandin H synthases, nonsteroidal antiinflammatory drugs and colon cancer", 1997 FASEB J.11:234-247.

Hixson, L. J. et al., "Antiproliferative effect of non-steroidal antiinfiammatory drugs against human colon cancer cells", 1994 Cancer Epidemiol Biomarkers Prev. 3:5:433-438.

Dubois. R. N. et al, "Nonsteroidal antiinfiammatory drugs, eicosanoids and colorectal cancer prevention", 1996 Gastroenterol Clin. N. Am. 25:773-791.

Watson, A J., "Chemopreventive effects of NSAIDs against colorectal cancer:regulation of apoptosis and mitosis by C0X-1 and COX-2", 1998 Histol Histopathol 13:591-597.

Steering Committee of the Physicians Health Study Research Group, "Final report on the aspirin component of the ongoing Physician Health Study", 1989 N. Engl. J. Med. 321:129-135.

Muscat, J. E. et al., "Nonsteroidal Antiinflammatory drugs and colorectal cancer", 1994 Cancer 74:1847-1854.

Giovannucci, E. et al., "Aspirin and the risk of colorectal cancer in women", 1995 N. Engl. J. Med. 333:609-614.

Giovannucci, E. et al., "Aspirin use and the risk of colorectal cancer and adenoma in male health professionals", 1994 Ann. Int. Med. 121:241-246.

Pollard, M. et al., "Effect of indomethacin on intestinal tumors induced in rats by the acetate derivative of dimethylnitrosamine", 1981 Science 214:558-559.

Reddy, B. S. et al., "Dose-related inhibition of colon carcinogenesis by dietary piroxicam, a nonsteroidal antiinflammatory drug, during different stages of rat colon tumor development", 1987 Cancer Res. 47:5340-5346.

Narisawa, T. et al., "Inhibition of development of methylnitrosurea induced rat colon tumors by indomethacin treatment ", 1981 Cancer Res. 41:1954-1957.

Kudo, T. et al., "Antitumor activity of indomethacin on methylazoxymethanol-induced large bowel tumors in rats", 1980 Gann. 71:260-264.

Caprie Steering Committee, "A randomised, blinded, trial of clopidogrel versus aspirin in patients at risk of ischaemic events (CAPRIE)" 1996 Lancet 348:1329-1339.

Dwerryhouse, S. J. et al., "Non-cytotoxic control of colorectal cancer", 1997 Royal College of Surgeons of Edinburgh 141-153.

Sokoloski, John A. and Sartorelli, Alan C., "Induction of the differentiation of HL-60 promyelocytic leukemia cells by nonsteroidal anti-inflammatory agents in combination with low levels of vitamin $D_3$ ", 1998 Leukemia Research 2:153-161 /.

Pence, Barbara C. et al., "Chemopreventive effects of calcium but not aspirin supplementation in cholic acid-promoted colon carcinogenesis: correlation with intermediate endpoints", 1995 Carcinogenisis 4:757-765.

Kristiansen, E., et al., "Influence of different diets on development of DMH-induced aberrant crypt foci and colon tumor incidence in Wistar rats", 1995 Nutr. Cancer 23, 151-159.

Díaz, Darío, et al., "Apoptosis is induced by the active metabolite of vitamin $D_3$ and its analogue EB1089 in colorectal adenoma and carcinoma cells :possible implications for prevention and therapy", 2000 Cancer research 60, 2304-2312.

Tsujiuchi T., et al., "Mutations of ademonatous polyposis coli and beta-catenin genes during progression of lung tumours induced by N-nitrosobis (2-hydroxypropyl) amine in rats", 2000 Cancer Res., 60:6611-6.

Sunaga, N., et al., "Constitutive activation of the Wnt signalling pathway by CTNNB1 (beta-catenin) mutations in a subset of human lung adenocarcinoma.", 2001 Genes Chromosomes Cancer 30:316-321.

Piyathilake, C. J. et al., "Localized folate and vitamin B-12 deficiency in squamous cell lung cancer is associated with global DNA hypomethylation", 2000 Nutr. Cancer 37:99-107.

Hirsch, F. R. et al., "Early detection of lung cancer: clinical perspectives of recent advances in biology and radiology", 2001 Clin. Cancer Res. 7:5-22.

Saha, D. et al., "Synergistic induction of cyclooxygenase-2 by transforming growth factor-beta1 and epidermal growth factor inhibits apoptosis in epithellal cells", 1999 Neoplasia1 508-517.

Kim, T. et al., "Alteration of cell growth and morphology by overexpression of transforming growth factor beta type II receptor in human lung adenocarcinoma cells", 2001 Lung cancer 31:181-191.

Marrogi, A. J. et al., "Nitric oxide synthase, cyclooxygenase 2 and vascular endothelial growth factor in the angiogenesis of non-small cell lung carcinoma", 2000 Clin. Cancer Res. 6:4739-4744.

Hosomi, Y. et al., "Increased cyclooxygenase 2 (COX-2) expression occurs frequently in precursor lesions of human adenocarcinoma of the lung", 2000 Lung Cancer 30:73-81.

Shirharama, T., "Cyclooxygenase-2 expression is up-regulated in transitional cell carcinoma and its preneoplastic lesions in the human urinary bladder", 2000 Clin. Cancer Res. 6:2424-2430.

Ristimaki, A. et al., "Expression of cyclooxygenase-2 in human transitional cell carcinoma of the urinary bladder", 2001 Am. J. Pathol. 158:849-853.

Rioux, N. et al., "The induction of cyclooxygenase-1 by a tobacco carcinogen in U937 human macrophages is correlated to the activation of NRF-kB", 2000 Carcinogenesis 21:1745-1751.

Witschi, H. et al., "Chemoprevention of tobacco-smoke lung carcinogenesis in mice after cessation of smoke exposure", 2000 Carcinogenesis 21:977-982.

Montoya, R. G. et al., "Chemoprevention of gastrointestinal cancer", 1997 Cancer and Metastasis Reviews 16:405-419.

Pence, B.C.et al., "Experimental chemoprevention of colon carcinogenesis by combined calcium and aspirin", 1994 Proceedings of the American Association for Cancer Research 35: 624.

Niv, Y. et al., "In Colorectal Carcinoma Patients, Serum Vitamin D levels vary according to stage of the carcinoma", 1999 Cancer 86:391-397.

Kahn, M. et al., "Chemoprevention for colorectal carcinoma", 1997 Hematol. Oncol. Clin. North Am. 11:779-794.

Walter T. Boone, Scientific Article, Journal MSMA, "Colorectal Cancer-Chemoprevention", pp. 318-322 (Sep. 1998).

Meggouh et al., J. Steroid Biochem., (1990) vol. 36, No. 1-2, pp. 143-147, Abstract Only.

Yang Kang et al., Transforming growth factor-$\beta1$ and its receptors in human lung cancer and mouse lung carcinogenesis, Experimental Lung Research, 26:685-707, 2000.

Robert A. Soslow et al., COX-2 is expressed in human pulmonary, colonic, and mammary tumors, Cancer, Dec. 15, 2000, vol. 89, No. 12, pp. 2637-2645.

Yao R. et al., Inhibition of COX-2 and induction of apoptosis: two determinants of nonsteroidal anti-inflammatory drugs' chemopreventive efficacies in mouse lung tumorigenesis, Exp. Lung. Res., 26(8):731-742 (2000) (Abstract only).

Witschi H., Successful and not so successful chemoprevention of tobacco smoke-induced lung tumors, Exp. Lung Res., 2000, Dec., 26(8):743-755 (Abstract only).

Rioux, N. et al., Prevention of NNK-induced lung tumorigenesis in A/J mice by acetylsalicylic acid and NS-398, Cancer Res., Dec. 1, 1998, 58(23):5354-5360, (Abstract only).

Caroline Duperron et al., Chemopreventive efficacies of aspirin and sulindac against lung tumorigenesis in A/J mice, Carcinogenesis, vol. 18, No. 5, pp. 1001-1006, 1997.

Hong, W. K., Biological effects and tolerability of celecoxib as a chemopreventive agent in current and former smokers; published in IARC Cancer Databases on www.iarc.fr.

Carlos Cordon-Cardo et al., Genetic and molecular markers of urothelial premalignancy and malignancy, Scand. J. Urol. Nephrol. Suppl. 205:82-93, 2000.

Mark L. Gonzalgo et al., Biological pathways to bladder carcinogenesis, Seminars in Urologic Oncology, vol. 18, No. 4 (Nov.), 2000:, pp. 256-263.

H. Wijkstrom et al., Prevention and treatment of urothelial premalignant and malignant lesions, Scand. J. Urol. Nephrol. Suppl. 205: 116-135, 2000.

Martin Komhoff et al., Short Communication, Enhanced expression of cyclooxygenase-2 in high grade human transitional cell bladder carcinomas, American Journal of Pathology, vol. 157, No. 1, Jul. 2000, pp. 29-35.

Castelao, J. E. et al., Non-steroidal anti-inflammatory drugs and bladder cancer prevention, Br. J. Cancer 2000, Apr., 82(7): 1364-1369 (Abstract only).

Rao, K. V. et al., Differential activity of aspirin, ketoprofen and sulindac as cancer chemopreventive agents in the mouse urinary bladder, Carcinogenesis, Jul. 1996, 17(7):1435-1438, (Abstract only).

Cohen, S. M. et al., Effect of aspirin on urinary bladder carcinogenesis initiated with N-[4-(5-nitro-2-furyl)-2thiazolyl] formamide in rats, Cancer Res. Jan. 1989, 15;49(2):372-377 (Abstract only).

Konety, B. R. et al., Effects of vitamin D (calcitriol) on transitional cell carcinoma of the bladder in vitro and in vivo, J. Urol., Jan. 2000, 165(1):253-258.

B. Prokopczyk et al., Chemoprevention of lung tumorigenesis induced by a mixture of benzo(a)pyrene and 4-(methylnitrosamino)-1-(3-pyridyl)-1-butanone by the organoselenium compound 1,4-phenylenebis(methylene)selenocyanate, Cancer Letters 161 (2000) 35-46.

Kirsten Pilegaard et al., Failure of the cultivated mushroom (*Agaricus bisporus*) to induce tumors in the A/J mouse lung tumor model, Cancer Letters 120 (1997) 79-85.

Stephen S. Hecht et al., Evaluation of butylated hydroxyanisole, myo-inositol, curcumin, esculetin, resveratrol and lycopene as inhibitors of benzo[a]pyrene plus 4-(methylnitrosamino)-1-(3-pyridyl)-1-butanone-induced lung tumorigenesis in A/J mice, Cancer Letters, 137 (1999) 123-130.

Chandrika J. Piyathilake et al., Localized folate and vitamin b-12 deficiency in squamous cell lung cancer is associated with global dna hypomethylation, Nutrition and Cancer, 37(1), 99-107.

Fred R. Hirsch et al., Early detection of lung cancer: clinical perspectives of recent advances in biology and radiology, Clinical Cancer Research, vol. 7, 5-22, Jan. 2001.

Debabrata Saha et al., Synergistic induction of cyclooxygenase-2 by transforming growth factor-$\beta1$ and epidermal growth factor inhibits apoptosis in epithelial cells, Neoplasia, vol. 1, No. 6, Dec. 1999, pp. 508-517.

Tae-Kyun Kim et al., Alteration of cell growth and morphology by overexpression of transforming growth factor $\beta$ type II receptor in human lung adenocarcinoma cells, Lung Cancer 31 (2001) 181-191.

Aizen J. Marrogi et al., Nitric oxide synthase, cyclooxygenase 2, and vascular endothelial growth factor in the angiogensis of non-small cell lung carcinoma, Clinical Cancer Research, vol. 6, 4739-4744, Dec. 2000.

Johansson, S. et al., Vitamin A antagonizes calcium response to vitamin D in man, J. Bone Miner Res., Oct. 2001, 16(10): 1899-1905 (Abstract only).

The Future of Prostate Cancer Prevention, Otis W. Brawley et al., Annals New York Academy of Sciences, 942, Published Dec. 2001, p. 145-152.

Klan, R. et al., Acetylsalicylic acid inhibition of n-butyl-(4-hydroxybutyl) nitrosamine-induced bladder carcinogenesis in rats, J. Cancer Res. Clin. Oncol., 1993; 119(8): 482-485, (Abstract only).

Belinsky, Steven A. et al., "The A/J Mouse Lung as a Model for Developing New Chemointervention Strategies" Cancer Research, Jan. 15, 1993, pp. 410-416, vol. 53.

Ohno, Joji et al., "Telomerase activation and p53 mutations in urethane-induced A/J mouse lung tumor development" Carcinogenesis, 2001, pp. 751-756, vol. 22, No. 5.

* cited by examiner

Number of Lung Tumours

| Mouse no. | Group A | Group B | Group C |
|---|---|---|---|
| 1 | 2 | 0 | 0 |
| 2 | 2 | 2 | 0 |
| 3 | 4 | 0 | 0 |
| 4 | 0 | 0 | 0 |
| 5 | 3 | 0 | 0 |
| 6 | 2 | 0 | 1 |
| 7 | 1 | 1 | 0 |
| 8 | 2 | 0 | 0 |
| 9 | 1 | 0 | 0 |
| 10 | 2 | 2 | 0 |
| 11 | 1 | 1 | - |
| 12 | 2 | - | 0 |
| 13 | - | 0 | 0 |
| 14 | 0 | 1 | 0 |
| 15 | 1 | - | 0 |
| 16 | 0 | 0 | 0 |
| 17 | - | 0 | 0 |
| 18 | 0 | 0 | 0 |
| 19 | 1 | 1 | - |
| 20 | 0 | 1 | 0 |
| Mean | 1,3 | 0,5 | 0,1 |
| Std.dev | 1,1 | 0,7 | 0,2 |

Fig.2

Number of Urinary Bladder Tumours

| Mouse no. | Group A | Group B | Group C |
|---|---|---|---|
| 1 | 1 | 0 | 0 |
| 2 | 2 | 0 | 0 |
| 3 | 1 | 0 | 0 |
| 4 | 1 | 0 | 0 |
| 5 | 0 | 0 | 0 |
| 6 | 0 | 0 | 0 |
| 7 | 1 | 0 | 0 |
| 8 | 0 | 0 | 0 |
| 9 | 0 | 1 | 0 |
| 10 | 0 | 0 | 0 |
| 11 | 0 | 0 | - |
| 12 | 0 | - | 0 |
| 13 | - | 0 | 0 |
| 14 | 0 | 0 | 0 |
| 15 | 0 | - | 0 |
| 16 | 0 | 0 | 0 |
| 17 | - | 0 | 0 |
| 18 | 0 | 0 | 0 |
| 19 | 0 | 0 | - |
| 20 | 0 | 1 | 0 |
| Mean | 0,3 | 0,1 | 0,0 |
| Std.dev | 0,6 | 0,3 | 0,0 |

Fig. 3

COMBINATION DOSAGE OF A CYCLOOXYGENASE (COX) INHIBITOR, A VITAMIN $D_3$ INCLUDING ANALOGUES AND METABOLITES THEREOF AND/OR CALCIUM FOR PREVENTION OF EPITHELIAL CANCER

CROSS-REFERENCE TO RELATED APPLICATIONS

This application is a national phase of PCT Application No. PCT/DK02/00231, filed on Apr. 5, 2002, which is a Continuation-in-Part of U.S. patent application Ser. No. 09/825,891, filed Apr. 5, 2001, now U.S. Pat. No. 6,703,380, which is a Continuation-in-Part of PCT Application No. PCT/DK00/00546, filed Sep. 29, 2000, which claimed priority from Denmark Application No. 1999 01390, filed on Sep. 29, 1999. This application is also a Continuation-in-Part of U.S. patent application Ser. No. 09/825,891, filed Apr. 5, 2001, now U.S. Pat. No. 6,703,380, which is a Continuation-in-Part of PCT Application No. PCT/DK00/00546, filed Sep. 29, 2000, which claimed priority from Denmark Application No. 1999 01390, filed on Sep. 29, 1999.

In recent years, focus is very much on cancer prevention, in acknowledgement of the fact that surgery mostly does not suffice as the only modality and that most cytotoxic regimens are ineffective against solid tumours. With the choices and results of treatment known today, only effective prevention will be able to reduce decisively epithelial cancer such as lung, bladder, prostate and gynecological cancer morbidity and mortality in a decisive manner.

The term chemoprevention covers the use of pharmacologically active, non-cytotoxic agents or naturally occurring nutrients that protect against the emergence and development of clones of mutated, malignant cells.

The present invention relates to use of a cyclooxygenase (COX) inhibitor, vitamin $D_3$ including analogues and metabolites thereof or calcium as well as combinations thereof for the preparation of a medicament for chemoprevention of epithelial cancer, such as lung, bladder, prostate and gynaecological carcinogenesis. In a further aspect the invention relates to a method for reducing the effective dosage of a cyclooxygenase (COX) inhibitor such as acetylsalicylic acid (ASA) in a chemopreventive treatment of epithelial cancer, such as lung, bladder, prostate and/or gynecological cancer in a human by co-administration with a non toxic dosage of a vitamin $D_3$ including analogues and metabolites thereof and, if so desired, Ca. In a presently preferred embodiment the invention relates to the use of ASA, a vitamin $D_3$ and calcium together with a pharmaceutically acceptable carrier for the preparation of a medicament for preventing the initiation and/or progression of epithelial cancer, such as lung, bladder, prostate and/or gynaecological cancer in a human. The invention also relates to such pharmaceutical medicaments.

BACKGROUND

Calcium

Calcium salts are used mainly in the treatment of calcium deficiency. Hypocalcaemia, a decrease in plasma-calcium concentration below the normal range, may be due to reduction in dietary intake, impaired or reduced absorption from the gastrointestinal tract, increased deposition in bone, or to excessive losses. Other causes of hypocalcaemia include decreased parathyroid hormone activity, vitamin D deficiency, and hypomagnesaemia.

Pharmacokinetics and Dynamics

Calcium is absorbed from the small intestine and vitamin D stimulates this absorption. About one-third of ingested calcium is absorbed although this can vary depending on dietary factors and the state of the small intestine; also, the absorption is increased during periods of high physiological requirement such as during pregnancy and lactation.

After absorption calcium is eventually incorporated into bones and teeth with 99 percent of the body's calcium content being present in such skeletal tissue. The remaining calcium is present in both the intra- and extracellular fluids. About 50 percent of the total blood-calcium content is in the physiologically active ionised form with 5 percent being complexed to citrate, phosphate, or other anions and 45 percent being bound to proteins. The amount of calcium in the intestinal lumen binds free fatty acids and secondary bile acids by saponification and reduces the local irritant effect of these acids in the colon.

Excretion of calcium occurs in the urine although a large proportion is reabsorbed in the renal tubules. Excretion also occurs in the faeces, this consisting of unabsorbed calcium as well as that secreted in the bile and pancreatic juice. Minor amounts are lost in the sweat. Calcium crosses the placenta and is also excreted in breast milk.

Mechanisms of Action

In recent years focus has Increasingly been directed at the central role of calcium in intra- and intercellular signal transduction.

Calcium is a key factor in maintaining normal cell membrane function, and calcium flux over the cell membrane plays a central role in mediating intracellular signal transduction regulating multiple cellular functions. Furthermore, the expression of cellular surface cadherins, which are necessary to maintain Intercellular contact, depends on the presence of calcium. Thus, calcium apparently has an important role in the structure and dynamics of the cellular actin-cytoskeleton.

Reduction of calcium concentration in intercellular fluid lowers cell response to growth regulating factors and reduces the permeability of cell membranes. When the calcium concentration is reduced, the rates of proliferation and dedifferentiation increase. Proliferative signals from low extracellular calcium are emitted via increased expression of c-myc.

Calcium contributes to the regulation of all cell division and cell differentiation phases, primarily through activation of various protein kinases (cAMP dependent kinase, Ca-calmodulin dependent protein kinase, protein kinase C).

Administration

The recommended daily allowance (RDA) of calcium is 800 to 1200 mg daily, increasing to 1500 mg daily for the elderly.

Recommended dosage of calcium depends on the patient's disorder. In dietary deficiency and as adjunct to osteoporosis therapy doses of 1000 to 1500 mg daily are recommended. Osteomalacia is usually treated with 1000 to 3000 mg of calcium.

1,25-dihydroxycholecalciferol (Calcitriol)

Vitamin D compounds are fat-soluble sterols, whose active metabolites are considered to be hormones, which are essential for proper regulation of calcium and phosphate homeostasis and bone mineralisation.

Toxicity

Excessive intake of vitamin D leads to the development of hypercalcaemia and its associated symptoms including anorexia, nausea, vomiting, weakness, fatigue, and headache. Interindividual tolerance to vitamin D varies considerably; infants and children are generally more susceptible to its toxic effects. Milk-alkali syndrome with hypercalcaemia is a rare possibility in chronically treated individuals.

Certain synthetic vitamin $D_3$ analogue preparations have proved to have 100 to 200 times the anti-proliferative effect and effect on differentiation and only 0.5 times the hypercalcaemic effect of 1,25-dihydroxycholecalciferol (H. H. Raskov, 1999, not published, Zhou et al., 1991 and Evans et al., 2000).

Pharmacokinetics and Dynamics

Vitamin D substances are well absorbed from the gastrointestinal tract. The presence of bile is essential for adequate intestinal absorption; absorption may be decreased in patients with decreased fat absorption.

Vitamin D and its metabolites circulate in the blood bound to a specific α-globulin. Vitamin D can be stored in adipose and muscle tissue for long periods of time. It is slowly released from such storage sites and from the skin where it is formed in the presence of sunlight or ultraviolet light. Vitamin D compounds generally have a slow onset and a long duration of action; the newer analogues and metabolites, however, have a more rapid action and shorter half-lives.

Cholecalciferol (vitamin $D_3$) is hydroxylated in the liver to form 25-hydroxycholecaliferol $D(25(OH)D_3)$. This compound undergoes further hydroxylation in the kidneys to form the active metabolite 1,25-dihydroxycholecalciferol ($1\alpha,25(OH)_2D_3$). Further metabolism also occurs in the kidneys.

Vitamin D compounds and their metabolites are excreted mainly in the bile and faeces with only small amounts appearing in the urine; there is some enterohepatic recycling but it is considered to have a negligible contribution to vitamin D status. Certain vitamin D substances may be excreted into breast milk.

Vitamin D increases serum calcium by facilitating the absorption of calcium and phosphate from the intestinal canal as well as mobilising calcium from bones. It is known from studies of bone mineral turnover that vitamin D and calcium are mutually dependent factors, and this has also proved to be the case in the regulation of cell division and cell differentiation.

Mechanisms of Action

In addition to similarities in structure, metabolism and action to steroid hormones, vitamin D also crosses the cellular plasma membrane by diffusion and binds to specific cytoplasmic receptors (vitamin D receptor, VDR). Upon binding and activation this hormone-receptor complex is transported into the cell nucleus, where it activates transcription and subsequent protein synthesis.

A vitamin D receptor specific for the active metabolite of vitamin $D_3$ 1,25-dihydroxycholecalciferol has been found in the cytoplasm of a wide variety of tissue and cells. After binding to the receptor, the ligand-receptor complex is translocated into the nucleus where it complexes with the RXR (Retinoic X Receptor). This VDR-RXR hetereomer binds to promoter regions of cell cycle regulating genes containing a vitamin D response element.

The cyclin-dependent kinase inhibitor (Cki) $p21^{Waf-1/Cip-1}$ is one of the genes regulated in this way. It regulates the cell cycle by inhibition of the cyclin dependent kinases (Cdk) and thereby preventing cells passing from the G1 to the S phase. 1,25-dihydroxycholecaliferol also modulates c-myc, c-fos and c-jun oncogenic expression and presumably induces apoptosis.

Besides 1,25-dihydroxycholecalciferol, proliferation and differentiation is also regulated by the growth factors transforming growth factor, TGF and epidermal growth factor, EGF via SMAD signal proteins and VDR. This allows for exchange of signals between vitamin D and TGF and EGF signalling pathways (cross talk). At increased EFGR activation VDR is down-regulated.

1,25-dihydroxycholecalciferol increases intracellular calcium and stimulates various protein kinases by increased tyrosine phosphorylation and activation of various signal transmission systems. 1,25-dihydroxycholecalciferol stimulates transcription of the calbindin D gene in colonocytes, which is believed to increase transcellular calcium absorption.

Administration

A dose of 10 μg (400 IU) cholecalciferol (vitamin $D_3$) is usually sufficient in adults for the prevention of simple deficiency states. Deficiency due to malabsorption states or liver disease often requires higher doses for treatment of up to 1 mg (40,000 IU) daily.

The 1,25-dihydroxycholecalciferol (calcitriol) metabolite of cholecalciferol is often given as an initial adult dose of 0.25 to 2 μg daily, increased if necessary to a maximum of 3 μg daily.

Cyclooxygenases (COX)

The two identified isomeric forms of the COX enzymes, COX-1 and COX-2, catalyse the rate-limiting step in the synthesis of prostaglandin and therefore also known as prostaglandin synthases. The COX-1 is expressed as a constitutive active enzyme in virtually all tissues. In the upper gastrointestinal tract it affects the mucosa barrier by inducing bicarbonate secretion and mucin production primarily through prostaglandin E (PGE). PGE is quantitatively the dominant product of the turnover of arachidonic acid induced by COX-1.

Apart from the brain and kidneys where COX-2 is constitutive active, COX-2 is an inducible enzyme. Particularly, COX-2 is induced by inflammatory stimuli, it catalyses the formation of pro-inflammatory cytokines, including $PGE_2$ and $PGF_\alpha$ which induce proliferation, suppress the immune system and stimulate angiogenesis.

The substrate for the COX-2 enzyme is arachidonic acid which is metabolised via three different pathways (see FIG. 1): via the COX pathway to eicosanoids, which stimulate cell division, as observed in inflammatory conditions, or via the lipoxygenase pathway to hydroperoxides (HPETE) and hydroxy compounds (HETE). The third pathway for arachidonic add metabolism is via cytochrome P450 to HETE and EET (epoxyeicosatrienic acid).

Several classic carcinogens are used as electron donors during the COX catalysed reaction and are thereby activated (these agents have high DNA affinity). Among these carcinogens are polycyclic aromatic hydrocarbons, aflatoxins, halogenated pesticides, aromatic amines and phenol compounds. Thus, COX activates potential carcinogens into active metabolites harmful to the DNA.

The exact biochemical and cellular mechanisms underlying the preventive effect of COX inhibitors is only partially understood, but is considered to be closely related to the impact these drugs have on arachidonic acid metabolism and prostaglandin synthesis.

Mechanisms of Action

The COX inhibitor acetylsalicylic acid (ASA) (e.g. Aspirin) and its metabolite salicylate block the formation of prostaglandin from arachidonic acid by irreversible acetylation of COX, thereby preventing arachidonic acid access to the active part of the enzyme. The COX activity can only be re-established through production of new COX molecules, and cells without protein synthesis, such as platelets, are therefore unable to regain COX activity. The predominant chemopreventive effect of ASA is deemed to be COX-2 inhibition, which results in metabolism of arachidonic acid via a lipoxygenase pathway to 15-HETE (leucotriene with anti-inflammatory and antimitogenic effects), see FIG. 1. Most other NSAIDs (e.g. piroxicam, sulindac and indomethacin) exhibit reversible and dose-dependent blockage of COX. This makes ASA a more potent inhibitor of prostaglandins. As it appears from the above, however, there are several mechanisms of action. The prostaglandin cascade also depends on the calcium-regulated signal transmission system.

NSAID has been shown to inhibit several endonucleases; these are enzymes that cleave DNA molecules. Presumably they play a central part in the genomic instability that is one of the characteristics of epithelial multistep carcinogenesis (Hanif et al., 1995). Other molecular biology mechanisms are discussed in detail in (Kahlenberg et al., 1998).

Other proneoplastic effects of COX include changing $TGF_\beta$ from an anti-proliferative into a pro-proliferative growth factor, reducing intercellular and cellular-stromal contact and communication, and stimulating of angiogenesis and metastasis (Hanif et al., 1995).

The COX-1 protein contain three domains (COX domain, EGF like domain and membrane binding motif), of which one resembles the EGF (and also $TGF_\alpha$, which belongs to the EGF family). Inhibition of COX-1 is also associated with anti-angiogenesis, although to a lesser extent than COX-2 inhibition (DuBois, RN, personal communication).

The above mentioned properties of the COX isoforms seem to indicate that inhibition of both isoforms (COX-1 and COX-2) may be of importance to achieve optimum prevention.

The most frequent undesirable effects connected with long-term administration of NSAIDs are gastroduodenal ulceration and bleeding because of low PG and thromboxane $A_2$ levels in the gastrointestinal tract. PG stimulates mucin production and bicarbonate secretion, and thromboxane $A_2$ indicates platelet aggregation. These complications are primarily related to inhibition of the constitutive $COX_1$ enzyme.

Undesirable effects and complications primarily relate to the use of NSAIDs as analgesic or anti-inflammatory agents in significantly higher doses, but they are potential sequels after long-term use also in lower doses.

A review of 16 cohort studies and case-control studies showed that the risk of developing severe NSAID-induced gastrointestinal undesirable effects amounts to 2 to 4 percent a year at analgesic and anti-inflammatory daily doses. In low-dose aspirin prophylaxis of cardiovascular disease the relative risk-reduction in relation to stroke, acute myocardial infarction and/or cardiovascular death was found to be approx. 25%.

The Physicians' Health Study (325 mg of acetylsalicylic acid qod) found that, in addition to a significant reduction of the risk of acute myocardial infarct, there were significantly more cases of melaena and epistaxis than in the placebo group, but of neither cerebral haemorrhage nor unspecific gastrointestinal bleeding (including haematemesis).

There exist numerous data on the pharmacokinetics and toxicity of COX inhibitors, especially regarding ASA. The FDA has found that for instance acetylsalicylic acid is a safe and efficient anti-inflammatory and analgesic agent and well suited for over-the-counter sales. No further toxicological studies are necessary to assess the usage of acetylsalicylic acid in chemoprevention.

Lung Cancer

Lung cancer is one of the most prevalent and lethal cancers (USA>160,000 deaths, EU>150,000). More than 90 percent are caused by exposure to tobacco smoke (on virtually all instances cigarette smoking). There are four distinct histological types:

| | | |
|---|---|---|
| Small cell carcinoma | 20% | |
| Adenocarcinoma | 35% | Non Small Cell Lung Cancer |
| Squamous cell carcinoma | 30% | Non Small Cell Lung Cancer |
| Large cell carcinoma | 15% | Non Small Cell Lung Cancer |

5-year survival for NSCLC is 10%, for SCLC 3%. Surgery and chemotherapy have virtually no impact on the mortality. Only primary prevention will have an impact on survival.

Animal Models

Animal models of lung cancer are using either chemically induced carcinogenesis (i.e. nitrosamines, benzopyrenes) or genetically engineered models (i.e. p53 transgenic rodents). The chemically induced carcinogenic models are excellent study systems as they mimic the genetics and molecular biology of human lung cancer (Kang Y et al., 2000). One of the characteristics of human lung cancer development is the histological adenoma-carcinoma sequence from normal epithelia through a typical hyperplasia, early adenoma, late adenoma to invasive carcinoma. Many of the mutations in gene and down-stream effects are identical to other forms of solid cancers, i.e. mutations In K-ras, APC, MCC, p53 also seen in epithelial cancer. Essential signalling pathways also identical in these types of cancer, i.e. the wnt-, and EGFR pathways (Sunuga N et al., 2001, Tsujiuchi, T et al., 2000).

COX Expression in Lung Cancer

Increased COX-2 expression has been found in human lung cancer (Soslow R A et al., 2000). The inhibition of COX in animal settings is associated with conflicting results: COX inhibition (ASA) in a mouse model resulted in an increase in apoptotic index but no impact on number of K-ras mutations (Yao R. et al, 2000).

COX inhibition (ASA) in a mouse model (A/J) showed no effect (Witschi H., 2000).

In another study of COX2 inhibition in A/J mouse model ASA and NS-398 treatment decreased the mean of the lung tumor volumes (Rioux N et al., 1998). A study comparing the chemopreventive efficacies of aspirin and sulindac against tumorgigenesis in A/J mice concluded that salicylate and sulindac could be equally effective as chemopreventive agents (Duperron, C. et al., 1997)

So far only 5 chemopreventive studies in human populations have been identified by the IARC (International Agency for Research of Cancer, Lyon, France):

1 beta-carotene+retinal

2 Retinol

3 COX2 Inhibition (Celebra, Pharmacia)

4 Lipoxygenase inhibition (Zileutenin)

5 N-acetylcysteine

The study on COX2-inhibition is entitled Biological Effect and Tolerability of Celecoxib as a Chemopreventive Agent in Current and Former Smokers by Hong, W. K is a randomised placebo-controlled biomarker-based clinical trial in current and former smokers examining the effect of the COX-2 inhibitor celecoxib on biomarkers of lung cancer risk and COX-2 dependent signaling pathways. (Hong, W. K.)

None of the above studies have been terminated (termination 2002-2005) and there is so far no indication of effective chemoprevention against lung cancer.

Bladder Cancer

The annual incidence is about 23/100,000 inhabitants (36/100,000 men and 10/100,000 women). Five-year survival rate is 40-66 percent. 40% of the patients with CIS develop invasive cancer within 5 years. Tobacco (primarily cigarette) smoking accounts for 30-40 percent of all bladder cancers. Other risk factors are occupational exposure to rubber, organic dye and metal refining, cyclophosphamide, schistosomal infection and genetic predisposition ex. HNPCC (2%) Frequently involved genes/mutations/growth factors are p16, p53, c-myc, k-ras, EGF, Rb., COX2 (Cordon-Carlo, C. et al. 2000, Gonzalgo, M L et al. 2000, Wijkström, H. et al., 2000, Kömhoff, M. et al., 2000).

More than ninety percent are transitional cell carcinomas, 8 percent squamous cell carcinomas and 2 percent adenocarcinomas. Papillary urothelial hyperplasia is an early intermediate biomarker for transitional cell bladder cancer Present treatment of Ta and T1 tumours is TURB. Tumours are low grade and superficial. 50-70 percent recur locally within 6-12 months. For Tcis treatment is intravesical BCG installation or surgery (resection/cystectomy), whereas for T2-T4 tumours the treatment is resection/cystectomy.

Animal Models

The most frequent animal models are the carcinogen stimulated rodent models using either male B6D2F1 mice or female F344 Fischer rats.

Literature Search

A search in the National Library of Medicine using the PubMed on bladder neoplasia (BN) and chemoprevention (CP) revealed an epidemiological study on NSAIDS, primarily on Phenacetin (OR=0.81) (Castelao et al., 2000). According to IARC no ongoing chemopreventive studies in human bladder cancer populations are registered.

Searching the National Library of Medicine using the PubMed on Bladder neoplasms and aspirin a small body of data revealing conflicting evidence is found. In the literature aspirin is referred to as both an active chemopreventive agent (Klan R. et al., 1993), as an inactive agent (Rao et al., 1996), and even as an active promotor for carcinogenesis (Cohen et al., 1989).

When looking at bladder neoplasms and cholecalciferol one cell-line study on 253j and T-24 cell lines results in significant reduction in proliferation and induction of apoptosis (Konety et al., 2001).

Focusing on existing literature on bladder neoplasms it all concentrate on bone metabolism, hypercalcaemia, bone metastasis with no reference to epidemiology and prevention.

In conclusion there are no data in the existing literature to active chemoprevention of bladder neoplasm with reference to a combination of a COX inhibitor, cholecalciferol or its metabolites or calcium.

BRIEF DESCRIPTION OF THE INVENTION

No prospective, randomised, double-blind studies on prevention of epithelial cancer such as lung, bladder, prostate and gynecological cancer based upon a cyclooxygenase (COX) inhibitor, vitamin $D_3$ including analogues and metabolites thereof or calcium as well as combinations thereof exist. Studies of cancer chemoprevention are extremely expensive, as these would require a very high number of individuals and many years of duration if the study endpoints were to be invasive cancer and cancer-related mortality. For these reasons there is an increasing tendency towards relying on epidemiological studies of intermediary endpoints, animal trials of genetically engineered or carcinogenically stimulated animal populations and biological models for examining different biomarkers (mutations, growth factors, etc).

The individual drugs exert their effects on specific areas of the carcinogenesis: modification of signal transduction and expression of oncogenes, reduction of the carcinogenic impact on colonic epithelium and intracellular and intercellular signal transduction, inhibition of COX enzymes and probably apoptosis.

Based on epidemiological, animal experimental, and molecular biology studies, it is hypothetically possible to achieve an additive or synergistic cancer-preventive effect of a combination of the three substances described herein.

By combining ASA, 1,25-dihydroxycholecalciferol (or an analogue vitamin D preparation) and calcium, an additive or synergistic effect is likely to be achieved. Therefore, concentrations of the individual preparations can be decreased and toxicity reduced to a negligible level. Furthermore, compliance is more easily achieved with a single preparation than with a combination of three different products.

According to the present invention, the epithelial cancer, such as the lung, bladder, prostate and gynecological cancer preventive effect of the preparations manifests itself by a significant reduction of the incidence and overall morbidity and mortality of epithelial cancer, such as lung, bladder, prostate or gynaecological cancer. To achieve this effect, however, it is believed to be important to take the preparation consistently as prophylaxis over a long time (probably more than one year), exactly as for the prevention of ischaemic heart disease and osteoporosis.

By combining ASA with Calcitriol 1,25DHC (or an analogue preparation) or with calcium, an additive or synergistic effect is achieved, so that the amounts of the individual drugs presumably are reduced and the toxicity thereby reduced to a negligible level. In a preferred embodiment, ASA is combined with both 1,25DHC (or an analogue preparation) and calcium.

The preparations could be combined as follows:

500 mg of Calcium
  (calcium carbonate 1250 mg) and/or
0.5 µg of 1,25DHC (or vitamin $D_3$ 400 IU or
  $D_3$ analogue, eg, 0.25 µg of calcitriol or
  0.005 µg of calcitriol/kg BW) and
75 mg of ASA or an analogues reversible or
  irreversible $COX_2$ Inhibitor The main requirements for a preparation designed for chemoprophylaxis include: low price, high compliance and ultra-low toxicity; it is assumed that by adding 1,25DHC and calcium the amount of COX inhibitor (ASA) can be reduced, so that the ASA-related undesirable effects can be reduced to a negligible level without reducing its action.

At first, in vivo studies of the effect of the above have been carried out in the form of animal experiments in collaboration with Pipeline Biotech A/S. The results of the studies are shown in Table 1.

As a chemopreventive effect has been demonstrated on epithelial cancer as evidenced by the results shown in the example of the present application demonstrating a highly significant effect of a combination of a cyclooxygenase inhibititor, vitamin D3 or an analogue or metabolite thereof and calcium on lung and bladder carcinogenesis, chemoprevention from the use of can also be expected on other epithelial cancers such as prostate cancer and gynaecological cancer carcinogenesis. By the term gynaecological cancer is meant a cancer selected from the group consisting of ovarian epithelial cancer, such as serous cystomas, mucinous cystomas, endometrioid tumors, clear cell tumors and unclassified tumors of the ovarie; endometrial cancer, such as ciliated adenocarcinoma, secretory adenocarcinoma, papillary or villoglandular, adenocarcinoma with squamous differentiation, adenoacanthoma, adenosquamous; and cervical cancer such as squamous cell (epidermoid carcinoma) and adenocarcinoma.

In human and in animal studies, the first steps in the multistep carcinogenesis characterizing cancer development in lung mucosa, urinary bladder mucosa and mucosal tissues of the reproductive system have many identical aspects to epithelial cancer with regard to pathology, involved genetic changes (mutations) and down-stream effects hereof irrespective in which of the above organs they arise.

Mutual events in molecular biology during carcinogenesis in the respiratory tract, gastrointestinal tract, urinary tract and reproductive system are seen in a range of different cellular mechanisms:

Genetic changes during early carcinogenesis: APC mutations and beta-catenin mutations (Tsujichi, T. et al., 2000, Sunage, N. et al., 2001), DNA hypomethylation (Piyathflake, C J. et al., 2000), p53 mutations (during promotion/progression)

Down-stream effects on growth-promoting oncogenes and growth factors: myc and ras upregulation (Hirsch, F R. et al., 2001), EGF overexpression (Saha, D. et al., 1999)

Down-stream effects on growth-inhibiting tumour suppresor genes and growth factors: reduced levels of expression of TGF-beta (Kim, T. et al., 2001)

Down-stream effects on enzyme expression and metabolism: COX2 overexpression (Marrogi, A J. et al., 2000, Hosomi, Y. et al., 2000, Shirharama, T., 2000, Ristimaki, A. et al., 2001), COX1 overexpression (Rioux, N. et al., 2000), increased PgE(2) synthesis Saha, D. et al., 1999, Rioux, N. et al., 2000)

In animal studies on lung cancer, non-steroidal anti-inflammatory agents (NSAID) are shown to counteract the carcinogenesis initiated by the lung-tumour producing chemicals (Witschi, H. et al., 2000).

Accordingly, the scope of the present invention encompasses methods of treatments directed towards chemoprevention for lung cancer carcinogenesis, urinary bladder carcinogenesis, prostate carcinogenesis and gynaecological cancer carcinogenesis, and pharmaceutical compositions as outlined above for the use therefor. To investigate the chemopreventive effect of the combination of a cyclooxygenase inhibitor, 1,25 Dihydroxycholecaliferol and calcium, research protocols were developed to conduct animal experimental trials using appropriate rodent models of chemically induced carcinogenesis well known to the person of skill in the art. The experimental rodent models are attractive because a substantial overlap exists between man and mouse/rat in the genetic alterations thought to be responsible for tumourigene-sis. An example of such a trial is a trial using the A/J mouse lung cancer model wherein the carcinogen stimulation is provided by a benzpyrene product delivered by a gastric tube with various combinations of ASA, 1,25 DHC and calcium. The intermediary endpoints are precursor lesions such as a typical adenomatous hyperplasia of the lung or urothelial dysplasia, papillary hyperplasia and/or papilloma.

DETAILED DESCRIPTION OF THE INVENTION

In one embodiment the invention relates to a method for reducing the effective dosage of ASA in a chemopreventive treatment of epithelial cancer, such as lung, bladder, prostate and gynaecological cancer in a human at risk by co-administration with a non toxic dosage of a calcitriol including analogues and metabolites thereof and/or Ca in the form of a combination dosage. This is due to the fact that it has surprisingly been shown that the addition of the calcitriol and calcium by synergy in action decrease the necessary dosage of acetylsalisylic acid in order to decrease the formation of abberant crypt foci in a rat model of epithelial cancer both with respect to size and numbers (see WO01/22974). In a presently preferred embodiment, the invention relates to a method for prevention of the initiation and/or progression of epithelial cancer, such as lung, bladder, prostate and gynaecological cancer in a human comprising administering to the human a combination dosage of a cyclooxygenase (COX) inhibitor, a calcitriol including analogues and metabolites thereof and calcium.

By chemopreventive effect is meant prevention of epithelial cancer, such as lung, bladder, prostate and gynaecological cancer or the initiation and/or progression of epithelial cancer, such as lung, bladder, prostate and gynaecological cancer and or the effect of reducing the formation of conditions being pre-malignant of lung, bladder, prostate or gynaecological cancer.

By a combination dosage according to the present invention is meant individual dosages for instance in one packet containing the relevant pharmaceuticals in appropriate dosages and accompanied by instructions for a treatment regimen according to the use and methods of the invention or a physical entity of two or more of the ingredients. The combination dosage may also comprise different COX inhibitors as well as different vitamin $D_3$ analogues and/or metabolites.

According to the present invention, it is believed that the administration of the combination dosage should be carried out regularly with an average daily dosage of the cyclooxygenase inhibitor corresponding to the inhibition of $COX_1$ and/or $COX_2$ provided by a dosage of ASA in the range of 50 mg to 500 mg, preferably in the range of 25 to 400 mg, more preferred of in the range of 50 to 300 mg, still more preferred in the range of 75 to 150 mg, such as in the range of 75 to 100 mg, e.g. measured by whole blood assays e.g. by the method disclosed in Ehrich, E. et al., 1999.

The combination dosage may further comprise a vitamin $D_3$ including analogues and metabolites thereof corresponding to the antiproliferative and/or cell differentiation effect of the vitamin $D_3$ metabolite 1,25 dihydroxycholecalcipherol in the range of 0.1 microgram to 2 microgram.

Any calcium in the combination dosage may preferably be in the range of 200 mg to 3500 mg such as calcium in the range of from 250 mg to 3000 mg, such as in the range of from 300 mg to 2500 mg, preferably in the range of 400 to 2000 mg, more preferred in the range of from 500 to 1000 mg, such as 750 mg.

As mentioned above, the treatment or prevention should be continued for a long period in order to give the best effect; however it is believed that a beneficial effect may be obtained after a treatment of at least 3 months. Accordingly, the administration is preferably continued for at least 6 months, such as at least for 1 year, preferably for at least 2 years. However, persons in high risk may be treated according to the present invention for the rest of their lives.

In an important aspect, the administration of the combination dosage results in the prevention of the initiation or progression of epithelial cancer exceeding the effect of the administration of any of the individual ingredients in the same daily dosage and in the same period.

In another aspect, the method according to the invention is one wherein the combination dosage has a preventive effect which is at least additive compared with the effect of the individual effective ingredients. In one embodiment, the preventive effect is at least synergistic compared with the effect of the individual effective ingredients.

An additive effect according to the invention may be calculated as an effect of the sum of prevention by each of the substances ASA, Vitamin $D_3$. and Ca, respectively or by an effect of the sum of prevention by the selection of two of the substances ASA, the Vitamin $D_3$, and the Ca and the preventive effect by the remaining substance.

By synergistic effect according to the present invention is preferably meant an effect which is higher than the additive effect as disclosed above.

The COX inhibitor may be any one acting on one or more of the mechanisms selected from non-selective, reversible or irreversible acetylation of COX, reversible or irreversible acetylation of $COX_2$, reversible or irreversible acetylation of $COX_2$, inhibition of angiogenesis, inhibition of arachidonic acid metabolism, blocking of AA metabolism, inhibition of the stimulation of proliferation stimulation from Epidermal Growth Factor, and stimulation of apoptosis. In a preferred embodiment, the COX inhibitor is primarily a $COX_2$ inhibitor. The preferred COX inhibitor is ASA.

The ASA is preferably acting by one or more of the following mechanisms: inhibiting of cell proliferation; inhibition of upregulation of pro-proliferative agents such as growth factors; modulation of signal transduction; and induction of apoptosis. Also inhibition of angiogenesis, and inhibition of arachidonic acid metabolism may be the target for the ASA. In a further aspect, the cyclooxygenase inhibitor acts by decreasing the formation of potential carcinogens into DNA harmful metabolites.

The vitamin $D_3$ including analogues and metabolites thereof are preferably acting by one or more of the following mechanisms: inhibition of cell proliferation; inhibition of DNA synthesis; modulation of signal transduction; induction of differentation; and induction of apoptosis.

In an important aspect of the invention, the vitamin $D_3$ is a synthetic analogue having an hypercalcaemiac effect of 0.5 of the hypercalcaemiac effect of 1,25 dihydroxycholecalcipherol. A number of synthetic vitamin D analogues suitable according to the present invention are disclosed herein. In order to substitute one vitamin $D_3$ analogue according to the present invention, the relevant dosage may be correlated to the effect of 1,25 dihydroxycholecalcipherol by reference to the antiproliferative effect which may be evaluated by methods well-known in the art, such as disclosed in Wargovich, M J. et al., 1987 and Eisnan, J A. et al., 1987 herein. Alternatively, PTH may be used for the comparison study, e.g. measured as disclosed In Johansson S. et al.; 2001.

According to the present invention, the active mechanism of the calcium is preferably an effect on the expression of cellular surface cadherins and/or intra- and extracellular signal transmission.

One very important aspect of the present invention is the finding that the method may reduce the risk of developing epithelial cancer, such as lung, bladder, prostate or gynaecological cancer in the individual human receiving the treatment by at least 10% or more compared to the effect obtained by any of the individual ingredients in the same dosage and in the same period of administration. The reduction may be at least 20% or more, and in certain circumstances e.g. for high risk patients even 30% or more, preferably about 50%. The period used for measurement may be at least 3 months, such as at least 6 months, most preferred at least 1 year, such as at least 2 years.

One preferred combination dosage according to the invention is the combination dosage comprising ASA, 1,25 DHC and Ca in that these Ingredients are all well known drugs.

In a still further embodiment, the invention relates to the use of a vitamin $D_3$ and/or calcium together with a pharmaceutically acceptable carrier for the preparation of a medicament for preventing the initiation and/or progression of epithelial cancer in a human. In a preferred embodiment the medicament is in the form of a combination dosage comprising the vitamin $D_3$ and/or the calcium.

The use may be in accordance with any of the methods described above and in a still further embodiment, the invention relates to any such pharmaceutical medicament. The pharmaceutical medicament may accordingly comprise a combination of a cyclooxygenase (COX) inhibitor, a vitamin $D_3$ including analogues and metabolites thereof and/or calcium. In a further aspect, the pharmaceutical medicament is such a medicament in any of the disclosed combination dosages which is to be administered according to any of the methods described herein.

Accordingly, a further aspect of the invention relates to the use of a cyclooxygenase (COX) inhibitor, a vitamin $D_3$ including analogues and metabolites thereof and calcium together with a pharmaceutically acceptable carrier for the preparation of a medicament for preventing the initiation and/or progression of epithelial cancer in a human.

In a still further aspect, the present invention relates to a pharmaceutical medicament comprising a combination of a cyclooxygenase (COX) inhibitor, a vitamin $D_3$ including analogues and metabolites thereof and calcium in a combination dosage together with a pharmaceutically acceptable carrier.

The pharmaceutical medicament according to the invention is preferably a medicament wherein the combination dosage comprises vitamin $D_3$ including analogues and metabolites thereof corresponding to the antiproliferative and/or cell differentiation effect of the vitamin $D_3$ metabolite 1,25 dihydroxycholecalipherol in the range of 0.1 µg to 2 µg such as in the range of 0.2µ to 1.5 µg, preferably in the range of from 0.3 to 1 µg, more preferred in the range of from 0.4 µg to 0.75 µg, such as 0.5 µg.

In a further embodiment, the pharmaceutical medicament is one wherein the combination dosage comprises calcium in the range of 200 mg to 3000 mg, such as In the range of from 300 mg to 2500 mg, preferably in the range of 400 to 2000 mg, more preferred In the range of from 500 to 1000 mg, such as 750 mg.

In a preferred embodiment the pharmaceutical medicament according to the invention is one wherein the combination dosage comprises ASA in the range of 50 mg to 500 mg, preferably in the range of 25 to 400 mg, more preferred of in the range of 50 to 300 mg, still more preferred in the range of 75 to 150 mg, such as in the range of 75 to 100 mg, The most preferred medicament comprises 50 to 75 mg ASA, 500-1000 mg Ca, and 0.5 to 1 μg of 1,25 dihydroxycholecalcipherol.

Accordingly, in a preferred embodiment, the pharmaceutical is one pharmaceutical comprising all three ingredients in order to secure the right individual dosage and patient compliance.

In a preferred embodiment, the pharmaceutical is a fixed-dose pharmaceutical comprising all three ingredients in order to secure the correct dosage. The pharmaceutical should be administered once or twice per day.

In a preferred embodiment the $D_3$ vitamin has a limited Ca inducing effect on the Ca level. Accordingly, preferably the $D_3$ is a synthetic analogue having a hypercalcaemic effect of the most 0.5 of the hypercalcaemic effect of 1,25 dihydroxycholecalcipherol, calculated on a molar basis. This may be measured by methods known in the art. In the following relevant derivatives are disclosed.

In a still preferred embodiment, the vitamin $D_3$ analogues or derivatives are any one of the following disclosed in the references as mentioned.

WO 89/10351, which is hereby incorporated by reference, mentions the following vitamin D analogues:
A compound of the formula I

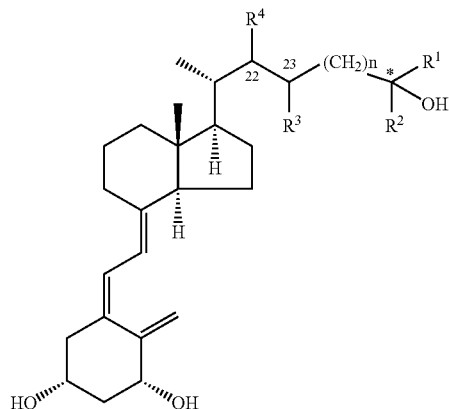

in which formula n is an integer from 1-7; and $R^1$ and $R^2$, which may be the same or different, represent for hydrogen, or straight or branched, saturated or unsaturated $C_1$-$C_7$-alkyl; with the provisos that when n=1, $R^1$ and $R^2$ cannot simultaneously be hydrogen, nor can $R^1$ and $R^2$ simultaneously be an alkyl group independently chosen from methyl, ethyl and normal-propyl, and when n=2, $R^1$ and $R^2$ cannot simultaneously be methyl; or $C_3$-$C_8$-cyclo-alkyl, or, taken together with the carbon (starred in formula I) bearing the hydroxyl group, $R^1$ and $R^2$ can form a saturated or unsaturated $C_3$-$C_8$ carbocyclic ring; and $R^3$ and $R^4$ represent either both hydrogen, or when taken together constitute a bond, such double bond (either in the Z or E configuration) connecting carbons numbered 22 and 23; and derivatives of the compounds of formula I In which one or more hydroxy groups have been transformed into —O-acyl or —O-glycosyl or phosphate ester groups, such masked groups being hydrolyzable in vivo, or derivatives of the compounds of formula I In which the hydroxyl group at the starred carbon atom is lacking, these compounds being converted to active compounds of formula I by enzymatic hydroxylation after administration.

In particular a diastereoisomer of a compound mentioned above, in pure form; or a mixture of diastereoisomers of a compound mentioned above.

Moreover, a compound according to the above mentioned specifications, selected from the group consisting of
1(S),3(R)-Dihydroxy-20(R)-(5-ethyl-5-hydrocy-1-heptyl)-9,10-secopregna-5(Z),7(E),10(19)-triene;
1(S),3(R-Dihydroxy-20(R)-(6-hydrocy-6-metyl-1-heptyl)-9,10-secopregna-5(Z),7(E),10(19)-triene;
1(S),3(R)-Dihydroxy-20(R)-(6-hydrocy-6-metylhept-1(E)-en-1-yl-9,10)-secopregna-5(Z),7(E),10(19)-triene;
1(S),3(R)-Dihydroxy-20(R-(6-ethyl-hydroxy-1-octyl)-9,10) secopregna-5(Z),7(E),10(19)-triene;
1(S),3(R)-Dihydroxy-20(R)-(7-hydrocy-7-metyl-1-octyl)-9,10)-secopregna-5(z),7(E),10(19)-triene;
1(S),3(R)-Dihydroxy-20(R)-(6'-metyl-1'-heptyl)-9,10-secopregna-5(Z),7(E),10(19)-triene;

WO 93/19044, which is hereby incorporated by reference, mentions the following vitamen D analogues:
A compound of the formula I

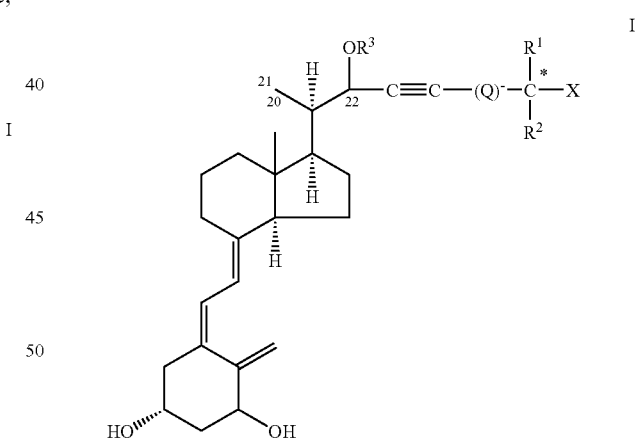

in which formula X is hydrogen or hydroxy; $R^1$ and $R^2$, which may be the same or different, stand for hydrogen or a $C_1$-$C_6$ hydrocrabyl radical; or $R^1$ and $R^2$, taken together with the carbon atom (starred in formula I) bearing the group X, can form a $C_3$-$C_8$ carbocyclic ring; $R^3$ stands for hydrogen or a $C_1$-$C_{10}$ hydrocarbyl radial or for $YR^4$, in which Y stands for the radicals —CO—, —CO—, —CO—S—, —CS—, —CS—O, —CS—S—, S—SO—OR—$SO_2$—, and $R^4$ stands for hydrogen or a $C_1$-$C_{10}$ hydrocarbyl radical; Qls a single bond or a $C_1$-$C_8$ hydrocarbylene diradical; $R^1$, $R^2$, $R^3$, and/or Q may be optionally substituted with one or more deuterium or fluorine atoms.

In particular a diastereoisomer of a compound mentioned above, in pure form; or a mixture of diastereoisomers of a compound mentioned above.

Moreover, a compound according to the above mentioned specifications, selected from the group consisting of
1(S),3(R)-Dihydroxy-20(R)-(1,5-dihydroxy-5-ethyl-2-heptyn-1-yl)-9,10-seco-pregna-5(Z),7(E),10(19)-triene;
1(S),3(R)-Dihydroxy-20(R)-(5-etyl-5-hydroxy-1-methoxy-2-heptyn-1-yl)-9,10-seco-pregna-5(Z),7(E),10(19)-triene;
1(S),3(R)-Dihydroxy-20(R)-(1-ethoxy-5-ehtyl-5-hydroxy-2-heptyn-1-yl)-9,10)-seco-pregna-5(Z),7(E),10(19)-triene;
1(S),3(R)-Dihydroxy-20(R)-(1-methoxy-4-hydroxy-4-ethyl-2-hexyn-1-yl)-9,10-seco-pregna-5(Z),7(E),10(19)-triene;
1(S),3(R)-Dihydroxy-20(R)-(1-ethoxy-4-hydroxy-4-ethyl-2-hexyn-1-yl)-9,10)-seco-pregna-5(Z),7(E),10(19)-triene;

isomer A.

WO 94/14766, which is hereby incorporated by reference, mentions the following vitamin D analogues:

A compound of the formula I

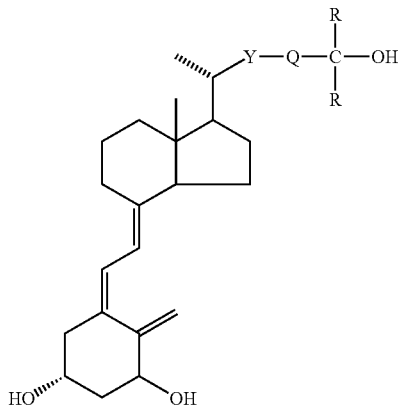

I in which formula Y Is sulfur, S(O), or S(O)$_2$; R represents C$_1$-C$_3$ alkyl; or

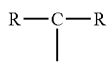

can form a C$_3$-C$_8$ carbocyclic ring; Q is a C$_1$-C$_8$ hydrocarbylene diradical; and prodrugs of I in which one or more of the hydroxy groups are masked as groups which can be reconverted to hydroxy groups in vivo.

A compound of the formula I shown above in which Y Is sulfur and Q is C$_2$-C$_4$-alkylene.

Moreover a stereoisomer of a compound according to the above mentioned specifications, in pure form; or a mixture of such stereoisomers.

Furthermore, a stereoisomer of a compound according to the above mentioned specifications having a saturated side chain with the R-configuration at C-20.

Furthermore, a compound according to the formula I which is
a) 1(S),3(R)-Dihydroxy-20(R)-(4-ethyl-4-hydroxy-1-hexylthio)-9,10-seco-pregna-S(Z),7(E),10(19)-triene,
b) 1(S),3(R)-Dihydroxy-20(R)-[5-methyl-5-hydroxy-1-hexylthio]-9,10-seco-pregna-S(Z),7(E),10(19)-triene,
c) 1 (S),3(R)-Dihydroxy-20(R)-[3-(1-methyl-1-hydroxy-ethyl)benzylthio]-9,10-seco-pregna-5(Z),7(E),10(19)-triene, or
d) 1(S),3(R)-Dihydroxy-20(R)-(3-methyl-3-hydroxy-1-butylthio)-9,10-seco-pregna-S(Z),7(E),10(19)-triene.

WO 93/0909, which is hereby incorporated by reference, mentions the following vitamin D analogues:
Compounds of general formulae (I) and (II)

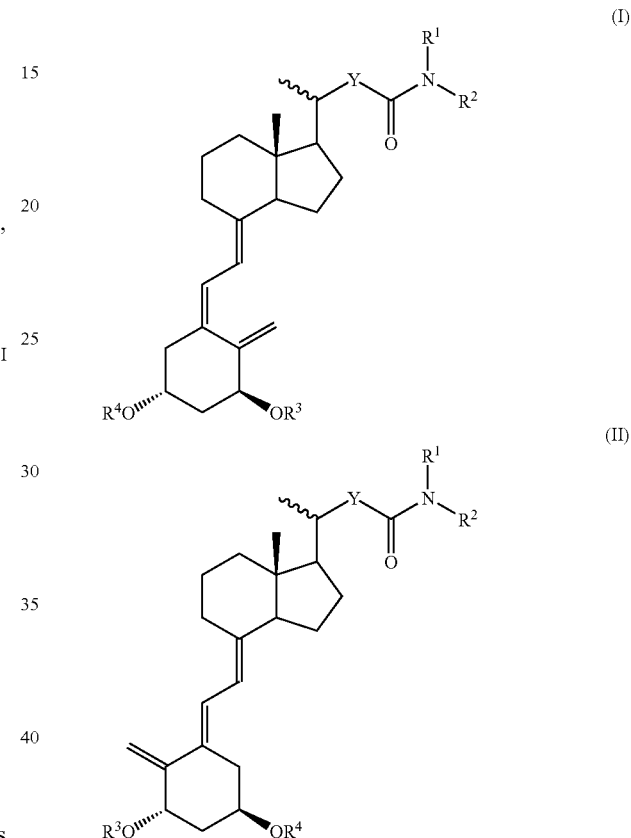

(wherein Y represents an alkylene or alkenylene group containing up to 4 carbon atoms; R$^1$ and R$^2$, which may be the same or different, each represents a hydrogen atom or a lower alkyl or cycloalkyl group or together with the nitrogen atom to which they are attached form a heterocyclic group; and R$^1$ and R$^4$, which may be the same or different, each represents a hydrogen atom or an O-protecting group).

Moreover compounds according to the above mentioned compounds wherein Y represents a group of formula

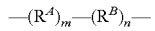

(wherein R$^A$ is —CH═CH—, R$^B$ is —CH$_2$, m is 0, 1 or 2 and n is 0 or an integer such that 2 m+n=1, 2, 3 or 4.

Furthermore, compounds according to the above mentioned compounds wherein Y is a C$_2$-C$_4$, alkylene group.

Compounds according to the above mentioned compounds wherein at least one of R$^1$ and R$^2$ is other than hydrogen.

Compounds according to the above mentioned compounds wherein R$^1$ and R$^2$ are selected from hydrogen atoms, methyl and cyclopropyl groups, or R$^1$R$^2$N— represents a piperidino group.

Compounds according to the above mentioned compounds wherein $R^3$ and $R^4$ represent etherifying silyl groups.

Compounds according to the above mentioned compounds wherein $R^3$ and $R^4$ are selected from hydrogen atoms and metabolically labile etherfying or esterifying groups.

Furthermore, the following compounds
1α,3β-dihydroxy-9,10-seco-25-azacholesta-5(Z),7,10(19) trien-24-one;
1α,3β-dihydroxy-23,23-bishomo-24-aza-9,10-secocholesta-5(Z),7,10(19)-trien-24-one;
1α,3β-dihydroxy-27-nor-9,10-secocholesta-5(Z),7,10(19), 22,24-pentaene-26-carboxylic acid, 26-dimethyl amide;
N,N-pentamethylene-1α,3β-dihydroxy-9,10-secocholanamide-5(Z),7,10(19)-triene;
N-cyclopropyl-1α,3β-dihydroxy-9,10-secocholanamide-5 (Z),7,10-(19)-triene;
1α,3β-dihydroxy-9,10-secocholanamide-5(Z),7,10(19)-triene;
N,N-pentamethylene-1α,3β-dihydroxy-9,10-seco-20-epi-cholanamide-5(Z),7,10(19)triene;

and corresponding 5(E)-isomers thereof.

WO 94/26707, which is hereby incorporated by reference, mentions the following vitamin D analogues:

Compounds of general formula (I)

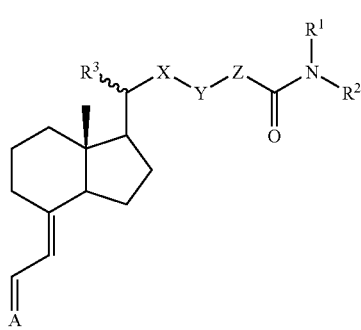
(I)

where $R^1$ and $R^2$, which may be the same or different, each represents a hydrogen atom or an aliphatic, cycloaliphatic, araliphatic or aryl group or together with the nitrogen atom to which they are attached form a heterocyclic group; $R^3$ represents a methyl group having α- or β-configuration; X represents a valence bond or a $C_{1-2}$ alkylene group; Y represents —O—, —S—, —CH— or —NR— where R is a hydrogen atom or an organic group; Z represents a valence bond or a $C_{1-3}$ alkylene group; and A=represents a cyclohexylidiene moiety characteristic of the A-ring of a 1α-hydroxylated vitamin D or analogue thereof, with the proviso that when X-Y-Z-together represent an alkylene group containing up to 4 carbon atoms, A=does not carry an exocyclic methylene group at the 10-position.

Compounds of the general formula (I) as shown above wherein A=represents one of the groups

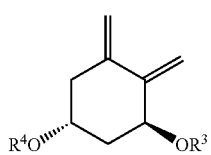
(A-2)

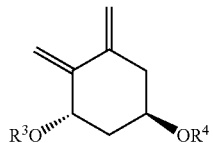
(A-3)

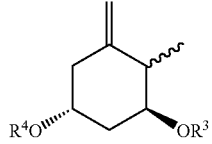
(A-4)

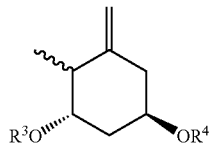
(A-5)

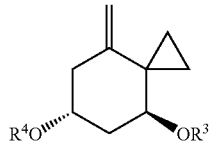
(A-6)

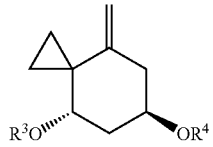
(A-7)
and

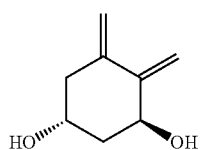
(A-8)

(where $R^4$ and $R^5$, which may be the same or different, each represents a hydrogen atom or an O-protecting group).

Moreover compounds of the general formula (I) and the specification mentioned above wherein $R^4$ and $R^5$ represent etherifying silyl groups.

Moreover compounds of the general formula (I) and the specification mentioned above wherein $R^4$ and $R^5$ are selected from hydrogen atoms and metabolically labile etherifying or esterif)ring groups.

Furthermore compounds of the general formula (I) according to the above specification wherein A=represents one of the groups

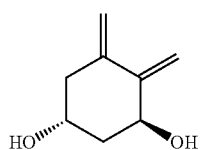
(A-2a)
and

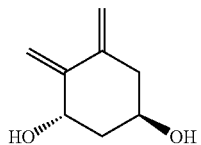

Compounds of the above general formula (I) wherein $R^1$ and $R^2$ are selected from hydrogen atoms, $C_{1-6}$ alkyl groups, $C_{3-8}$ cycloalkyl groups, $C_{6-12}$ aryl $C_{1-4}$ alkyl and optionally substituted $C_{6-12}$ carbocyclic aryl groups.

Compounds of the above-specked general formula (I) wherein $R^1$ and $R^2$ are selected from hydrogen atoms, $C_{1-6}$ alkyl groups and $C_{3-8}$ cycloalkyl groups.

Compounds of the above-specified general formula (I) wherein $R^1$ and $R^2$ are selected from hydrogen atoms, methyl, ethyl, and cyclopropyl groups.

Furthermore, the following compounds

1α,3β-dihydroxy-20-epi-22-oxa-9,10-secochola-5(Z),7,10(19)trienic acid, piperidine amide;

1α,3β-dihydroxy-20-epi-23-homo-22-oxa-9,10-secochola-5(Z),7,10(19)-trienic add, di-methylamine, cyclopropylamine and piperidine amides;

1α,3β-dihydroxy-20-epi-22-oxa-9,10-secochola-5(Z),7,10(19-trienic acid, morpholine amide;

1α,3β-dihydroxy-20-epi-23-bis-homo-22-oxa-9,10-secochola-5(Z),7,10(19)-trienic acid, piperidine amide;

1α,3β-dihydroxy-20-epi-23-homo-23-oxa-9,10-secochola5(Z),7,10(19)-trienic add, piperidine amide;

1α,3β-dihydroxy-23-homo-23-oxa-9,10-secochola-5(Z),7,10(19)-trienic acid, diethylamine, cyclopropylamine and piperidine amides and 20-epi analogues thereof;

1α,3β-dihydroxy-23-homo-23-oxa-9,10-secochola-5(Z),7-dienic add, diethylamine, cyclo-propylamine and piperidine amides and 29-epi analogues thereof:

1α,3β-dihydroxy-23-homo-23-oxa-10-spirocyclopropyl-9,10-secochola-5(Z),7-dienic acid, diethylamine, cyclopropylamine and piperidine amides and 20-epi analogues thereof;

1α,3β-dihydroxy-9,10-secochola-5(Z),7-dienic acid, piperidine amide;

1α,3β-dihydroxy-10-spirocyclopropyl-9,10-secochola-5(Z),7-dienic acid, piperidine amide;

1α,3β-dihydroxy-23-homo-9,10-secochola-5(Z),7-dienic acid, piperidine amide;

1α,3β-dihydroxy-23-homo-10-spirocyclopropyl-9,10-secochola-5(Z),7-dienic acid, piperidine amide;

1α,3β-dihydroxy-23-homo-19-nor-9,10-secochola-5,7-dienic add, piperidine amide;

1α,3β-dihydroxy-26-epi-23-homo-9,10-secochola-5(Z),7-dienic acid, piperidine amide;

1α,3β-dihydroxy-20-epi-23-homo-9,10-seco-23-thiachola-5(Z),7,10(19)-trienic acid, piperidine amide;

23-aza-1α,3β-dihydroxy-20-epi-23-bis-homo-9,10-secochola-5(Z),7,10(19)-trienic add, piperidine amide;

23-aza-1α,3β-dihydroxy-20-epi-23-homo-9,10-secochola-5(Z),7,10(19)-trienic acid, piperidine amide;

1α,3β-dihydroxy-20-epi-19-nor-9,10-secochola-5,7-dienic add, piperidine amide:

1α,3β-dihydroxy-23-homo-19-nor-23-oxa-9,10-secochola-5,7-dienic acid, piperidine amide;

23-aza-1α,3β-dihydroxy-9,10-secochola-5(Z),7,10(19)-trienic acid, piperidine amide;

22-aza-1α,3β-dihydroxy-20-epi-23-homo-9,10-secochola-5(Z),7,10(19)-trienic acid, piperidine amide;

23-aza-1α,3β-dihydroxy-9,10-secochola-5(Z),7,10(19)-trienic add, diethyl amide and the 20-epi analogue thereof;

1α,3β-dihydroxy-9,10-secochola-5(Z),7,10(19)-trienic acid, N-methyl-N-phenyl amide and the 20-epi analogue thereof; and 1α,3β-dihydroxy-9,10-secochola-5(Z),7-dienic acid, N-methyl-N-phenyl amide and the 20-epi analogue thereof.

WO 95/03273, which is hereby incorporated by reference, mentions the following vitamin D analogues:

Compounds of general formula (I):

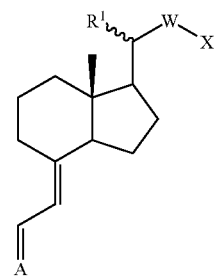

where $R^1$ represents a methyl group having α- or β-configuration; W represents a valence bond or a $C_{1-5}$ alkylene group; X represents azide or an optionally substituted triazole group; and A=represents a cyclohexylidene moiety characteristic of the A-ring of a 1α-hydroxylated vitamin D or analogue thereof.

Moreover compounds of the general formula (I) as shown above having the general formula (II)

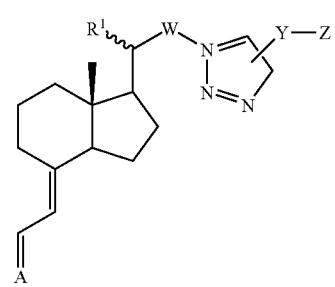

wherein $R^1$, W and A are as defined in claim 1; Y represents a valence bond or a lower alkylene group attached to the 4- or 5-position of the triazole ring; and Z represents either (I) a group —$CO.NR^2R^3$ in which $R^2$ and $R^3$ may be the same or different and are selected from hydrogen atoms, aliphatic, cycloaliphatic, araliphatic and aryl groups, or $R^2$ and $R^3$ together with the nitrogen atom to which they are attached form a heterocyclic group; or (II) a group —$(R^4)(R^5)$—OH in which $R^4$ and $R^5$ may be the same or different and are selected from hydrogen atoms, aliphatic, cycloaliphatic, araliphatic and aryl groups, or $R^2$ and $R^3$ together with the carbon atom to which they are attached form a $C_{3-8}$ carbocyclic ring.

Furthermore the compounds

20α-(3-azidopropyl)-1α,3β-dihydroxy-9,10-secopregna-5(Z),7,10(19)-triene;

20α-azido-1α,3β-dihydroxy-9,10-secopregna-5(Z),7,10(19)-triene;

1α,3β-dihydroxy-20α-[4-(2-hydroxyprop-2-yl)1,2,3-triazol-1-yl]-9,10-secopregna-5(Z),7,10(19)-triene;

1α,3β-dihydroxy-20α-[4-(3-hydroxypent-3-yl)-1,2,3-hiazol-1-yl]-9,10-secopregna-5(Z),7,10(19)-triene;

1α,3β-dihydroxy-20α-[4-(2-hydroxyprop-2-yl)-1,2,3-tdazol-1-ylmethyl]-9,10-secopregna-5(Z),7,10(19)-triene;

1α,3β-dihydroxy-20β-[4-(3-hydroxypent-3-yl)-1,2,3-triazol-1-ylmethyl]-9,10-secopregna-5(Z),7,10(19)-triene;

1α,3β-dihydroxy-20α-[4-(3-hydroxypent-3-yl)-1,2,3-triazol-1-ylmethyl]-9,10-secopregna-5(Z),7,10(19)-triene;

1α,3β-dihydroxy-20α-[4-(N,N-pentamethylenecarbamoyl)-1,2,3-triazol-1-ylmethyl]-9,10-secopregna-5(Z),7,10(19)-triene;

1α,3β-dihydroxy-20α-[4-(N,N-diethylcarbamoyl)-1,2,3-triazol-1-ylmethyl]-9,10-seco-pregna-5(Z),7,10(19)-triene;

1α,3β-dihydroxy-20α-[4-(N-cyclopropylcarbamoyl)-1,2,3-triazol-1-ylmethyl]-9,10-seco-pregna-5(Z),7,10(19)-triene;

1α,3β-dihydroxy-20α-[4-(N,N-3-oxapentamethylencarbamoyl)-1,2,3-triazol-1-ylmethyl]-9,10-secopregna-5(Z),7,10(19)-triene;

1α,3β-dihydroxy-20α-[4-(N,N-diisopropylcarbamoyl)-1,2,3-triazol-1-ylmethyl]-9,10-secopregna-5(Z),7,10(19)-triene;

1α,3β-dihydroxy-20β-[4-(N,N-pentamethylencarbamoyl)-1,2,3-triazol-1-ylmethyl]-9,10-secopregna-5(Z),7,10(19)-triene;

1α,3β-dihydroxy-20β-[4-(N,N-diethylcarbamoyl)-1,2,3-triazol-1-ylmethyl]-9,10-secopregna-5(Z),7,10(19)-triene;

1α,3β-dihydroxy-20β-[4-(N-cyclopropylcarbamoyl)-1,2,3-triazol-1-ylmethyl]-9,10-seco-pregna-5(Z),7,10(19)-triene;

1α,3β-dihydroxy-20β-[4-(N,N-3-oxapentamethylenecarbamoyl)-1,2,3-triazol-ylmethyl]9,10-secopregna-5(Z),7,10(19)-triene;

1α,3β-dihydroxy-20β-[4-(N,N-diisopropylcarbamoyl)-1,2,3-triazol-1-ylmethyl]-9,10-seco-pregna-5(Z),7,10(19)-triene;

1α,3β-dihydroxy-20α-{2-[4-(N,N-pentamethylenecarbamoyl)-1,2,3-triazol-1-yl]ethyl)-9,10-secopregna-5(Z),7,10(19)-triene;

1α,3β-dihydroxy 20α-(2-[4-(N,N-diethylearbamoyl)-1,2,3-triazol-1-yl]ethyl)-9,10-seco-pregna-5(Z),7,10(19)-triene;

1α,3β-dihydroxy-20α-(2-[4-(N-cyclopropylcarbamoyl)-1,2,3-triazol-1-yl]ethyl)-9,10-secopregna-5(Z),7,10(19)-triene;

1α,3β-dihydroxy-20α-{2-[4-(N,N-3-oxapentamethylenecarbamoyl)-1,2,3-triazol-1-yl]-ethyl)-9,10-secopregna-5(Z),7,10(19)triene;

1α,3β-dihydroxy-20α-(2-[4-(N,N-diisopropylcarbamoyl)-1,2,3-triazol-1-yl]ethyl)-9,20-seco-pregna-5(Z),7,10(19)-triene;

1α,3β-dihydroxy-20α-[4-(1-hydroxycyclohex-1-yl)-1,2,3-triazol-1-ylmethyl)-9,10-seco-pregna-5(Z),7,10(19)triene;

1α,3β-dihydroxy-20α-(2-[4-(3-hydroxypent-3-yl)-1,2,3-triazol-1-yl)ethyl)-9,10-secopregna-5(Z),7,10(19)-triene;

1α,3β-dihydroxy-20β{2-[4-(3-hydroxypent-3-yl)-1,2,3-triazol-1-yl]ethyl)-9,10-secopregna-5(Z),7,10(19)triene;

1α,3β-dihydroxy-20α-(3-[4-(3-hydroxypent-3-yl)-1,2,3-riazol-1-yl]propyl)9,10-secopregna-5(Z),7,10(19)-triene;

1α,3β-dihydroxy-20α-(3-[4-(3-methyl-3-hydroxybutyl)-1,2,3-triazol-1-yl)propyl)-9,10-seco-pregna-5(Z),7,10(19)-triene;

1α,3β-dihydroxy-20α-{3-[4-(2-methyl-2-hydroxypentyl)-1,2,3-triazol-1-yl)propyl]-9,10-seco-pregna-5(Z),7,10(19)-triene;

1α,3β-dihydroxy-20α-(3-[4-(4-ethyl-4-hydroxyhexyl]-1,2,3-triazol-1-yl]propyl)-9,10-seco-pregna5(Z),7,10(19)-triene;

1α,3β-dihydroxy-20α-{3-[4-(2-hydroxybut-2-yl)-1,2,3-triazol-1-yl]propyl)-9,10-secopregna-5(Z),7,10(19)triene;

1α,3β-dihydroxy-20α-{3-[4-(4-methyl-2-hydroxypent-2-yl)-1,2,3-triazol-1-yl)propyl)-9,10-secopregna-5(Z),7,10(19)-triene;

1α,3β-dihydroxy-20α-{3-[4-(2,4-dimethyl-3-hydroxypent-3-yl)-1,2,3-triazol-1-yl]propyl)-9,10-secopregna-5(Z),7,10(19)-triene;

1α,3β-dihydroxy-20α-[4-(2-ethyl-2-hydroxybutyl)-1,2,3-triazol-1-ylmethyl]-9,10-secopregna-5(Z),7,10(19)-triene;

1α,3β-dihydroxy-20α-[5-(2-ethyl-2-hydroxybutyl)-1,2,3-triazol-ylmethyl)-9,10-seco-pregna-5(Z),7,10(19)triene;

1α,3β-dihydroxy-20α-[4-(3-hydroxypent-3-yl)-1,2,3-triazol-1-ylmethyl]-9,10-secopregna-5(E),7-diene;

1α,3β-dihydroxy-20α-(3-hydroxypent-3-yl)-1,2,3-triazol-1-ylmethyl)-9,10-secopregna-5(Z),7-diene;

1α,3β-dihydroxy-20α-[4-(3-hydroxypent-3-yl)-1,2,3-triazol-1-ylmethyl]-10-spirocyclopropyl-9,10-secopregna-5(E),7-diene;

1α,3β-dihydroxy-20α-[4-(3-hydroxypent-3-yl)-1,2,3-triazol-1-ylmethyl)-10-spirocyclopropyl-9,10-secopregna-5(Z),7-diene;

1α,3β-dihydroxy-20α-[4-(3-hydroxypent-3-yl)-1,2,3-triazol-1-ylmethyl)-19-nor-9,10-seco-pregna-5,7-diene;

1α,3β-dihydroxy-20α-[4-(3-methyl-3-hydroxybutyl)-1,2,3-triazol-1-ylmethyl)-9,10-seco-pregna-5(Z),7,10(19) triene;

1α,3β-dihydroxy-20α-[4-(2-methyl-2-hydroxypentyl)-1,2,3-triazol-1-ylmethyl]-9,10-seco-pregna-5(Z),7,10(19) triene;

1α,3β-dihydroxy-20α-[4-(4-ethyl-4-hydroxyhexyl)-1,2,3-triazol-1-ylmethyl)-9,10-seco-pregna-5(Z),7,10(19) triene;

1α,3β-dihydroxy-20α-[4-(2-hydroxybut-2-yl)-1,2,3-triazol-1-ylmethyl]-9,10-secopregna-5(Z),7,10(19)triene;

1α,3β-dihydroxy-20α-[4-(4-methyl-2-hydroxypent-2-yl)-1,2,3-triazol-1-ylmethyl]-9,10-seco-pregna-5(Z),7,10(19) triene;

1α,3β-dihydroxy-20α-[4-(2,4-dimethyl-3-hydroxypent-3-yl)-1,2,3-triazol-1-ylmethyl]-9,10-secopregna-5(Z),7,10(19)-triene; and 1α,3β-dihydroxy-20α-[4-(2-hydroxypheneth-2-yl)-1,2,3-triazol-1-ylmethyl)-9,10-seco-pregna-5(Z),7,19(19) triene.

WO 95/02577, which is hereby incorporated by reference, mentions the following vitamin D analogues:

A compound of the formula

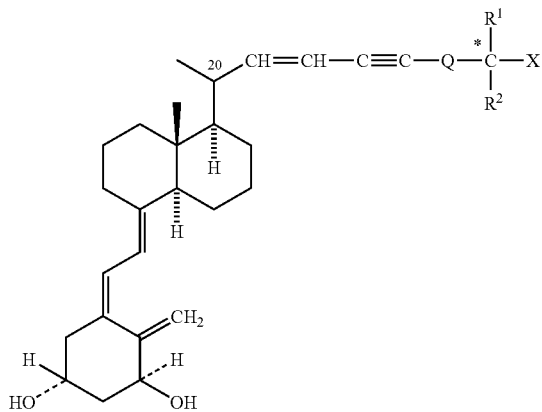

in which formula X is hydrogen or hydroxy; $R^1$ and $R^2$, which may be the same or different, represent hydrogen or $C_1$-$C_4$ hydrocarbyl; or $R^1$ and $R^2$, taken together with the carbon atom bearing the group X, can form a $C_3$-$C_8$ carbocyclic ring; Q is a single bond or a $C_1$-C4 hydrocarbylene diradical, the expression hydrocarbyl radical (hydrocarbylene diradical) indicating the residue after removal of 1 (2) hydrogen atom(s) from a straight, branched or cyclic saturated or unsaturated hydrocarbon; $R^1$, $R^2$ and/or Q may be optionally substituted with one or more fluorine atoms; and prodrugs of I in which one or more of the hydroxy groups are masked as groups which can be reconverted to hydroxy groups in vivo.

European patent application No. 0 205 025 A1, which is hereby incorporated by reference, mentions the following vitamin D analogues:

A compound of the formula (I)

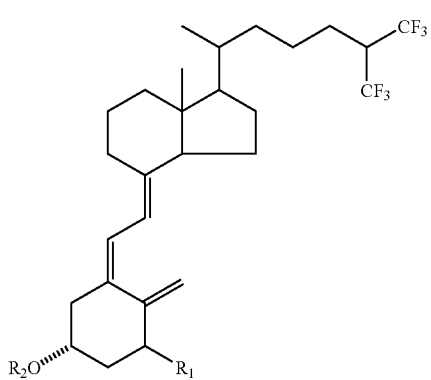

wherein $R_1$ is a hydrogen atom, a hydroxyl group or a protected hydroxyl group and $R_2$ is a hydrogen atom or a protecting group, such as 26,26,26,27,27,27-Hexafluoro-1α-hydroxyvitamin $D_3$.
26,26,26,27,27,27-Hexaflourovitamin $D_3$.

The COX inhibitors according to the invention in addition to the ASA include other NSAIDS known in the art.

Example

The objective of the present example is to investigate the chemopreventive effect of a combination of acetylsalicylic acid, 1α,25(OH)$_2$-vitamin $D_3$ and calcium on induced lung and urinary bladder tumorigenesis in A/J mice. Mice are chosen as the test model because of their suitability in this type of study. The A/J mouse induced with (B(a)P) and NNK is a scientifically recognized model of lung tumorigenesis (Prokopzyk et al., 2000, Pilegaard et al., 1997, Hecht et al., 1999).

Resumé:

At start of the experiment 60 female A/J mice are divided into 3 groups each of 20 mice. Group A mice are fed normal diet (5000 ppm calcium), Group B mice are fed a diet low in calcium (2500 ppm) and Group C mice are fed a diet containing 300 ppm acetylsalicylic acid, 0.02 µq/kg 1α,25(OH)$_2$-vitamin $D_3$ and 7500 ppm calcium. The three groups are fed on the three different diets in the entire experimental period.

After two weeks of feeding on the respective diets, tumorigenesis is induced in all 60 A/J female mice by peroral dosing of the lung carcinogens benzo(a)pyrene (B(a)P) and 4-(methylnitrosamino)-1-(3-pyridyl)-1-butanone (NNK) once a week for 10 consecutive weeks.

2 weeks after the last treatment with carcinogens, the mice are removed from the experiment. Lungs and bladders are prepared and the number of lung and bladder tumours are counted.

The results show that Group C, receiving 300 ppm acetylsalicylic acid, 0.02 µg/kg 1α,25(OH)$_2$-vitamin $D_3$ and 7500 ppm calcium, has a highly significantly reduced incidence of lung tumors, when compared to Group A, which is fed a standard diet (p<0.001). This finding applies to both the number of tumour-bearing animals and tumour multiplicity.

The same effect is observed on urinary bladder tumors, although at a less significant level (p<0.025) which is probably due to the lower number of tumors found in the urinary bladders.

Surprisingly, it is also found that the diet containing 2500 ppm of calcium has a chemopreventive effect on lung tumors when compared to the standard diet containing 5000 ppm of calcium (p=0.05). There is no apparent biologic rationale for this finding.

Materials and Methods

Inducers:
Benzo(a)pyrene (B(a)P), Aldrich Chem. Co., 3 µmol/mouse p.o.
4-(methylnitrosamino)-1-(3-pyridyl)-1-butanone (NNK), 3 µmol/mouse p.o.
Vehicle is cotton seed oil.
B(a)P and NNK are dissolved in cotton seed oil each at a concentration of 6 µmol/ml. The mice are dosed 0.5 ml p.o.

Experimental System:
60 female A/J mice are supplied by Taconic, N.Y., USA. At start of the acclimatization period the mice which have SPF status are 6 weeks of age.

The mice are caged in standard polypropylene cages (l×w×h=40×33×15 cm), 5 mice are caged together.

Bedding is Lignocel, produced by Hahn & Co., Faserstoffwerk, Bredenbeck-Kronsburg, Germany. Bedding is changed twice a week in a laminar flow unit. Cages are housed in an underpressured isolator with HEPA-filters (Class EU10, withholding 98.5% of all particles>0.3 µm. Temperature is 18° C.-22° C., and is controlled via the ambient ventilation system in the laboratory. Light cycle is 12-hour dark and 12-hour light (lights on 06.00).

Drinking water is UV sterilized. Water bottles are changed once a week during acclimatization and experiment.

Diets for the experiment are specifically manufactured by Altromin Denmark, "Brogården", Søbredden 27, 2820 Denmark.

Diet A is Altromin 1324 standard diet containing 5000 ppm Calcium

Diet B is Altromin 1324 standard diet containing 2500 ppm Calcium

Diet C is Altromin 1324 standard diet containing 300 ppm acetylsalicylic acid (Nycomed Denmark NS), 0.02 µg/kg $1\alpha,25(OH)_2$-vitamin $D_3$ (Leo Pharmaceuticals A/S, Denmark) and 7500 ppm calcium.

Diet is in the form of pellets and is irradiated as a mean of sterilization. Diet is administered ad libitum.

Animal Health and Welfare:

The mice have FELASA SPF-status and the housing and changing system is technically designed to preserve the SPF-status during the study. Mice are handled by educated personnel under veterinary supervision. Daily records and decisions are made concerning animal welfare.

Pre-Experimental Procedures:

Randomisation and Labelling:

On the day of arrival, the animals are randomly picked from the crates and successively allocated to 12 cages each containing 5 mice. The mice are individually labelled by ear punctures.

Acclimatisation and Health Procedures:

Mice are imported to the laboratory at the start up of the experimental procedure. No acclimatisation is needed since the mice are housed under preexperimental conditions for the first 2 weeks. Suppliers' Health Monitoring Report regarding the mice is checked and the mice are housed under conditions that preserve the SPF-status.

Experimental Procedures:

Upon arrival the mice are divided into 3 groups each of 20 mice. The groups are labelled A, B and C.

Group A is fed diet A.
Group B is fed diet B.
Group C is fed diet C.

The groups are fed these diets for the entire experimental period (16 weeks).

2 weeks after the last treatment with carcinogens, the mice are removed from the experiment. Lungs and bladders are prepared and the number of lung and bladder tumours are counted.

During the entire study period body weights, food consumption and drinking water consumption is determined for each group once a week.

Terminal Procedures:

2 weeks after the last treatment with carcinogens the mice are removed from the experiment and examined for presence of lung and bladder tumours.

Mice are euthanized and gross pathology is performed.

After pathology, the lungs are removed and fixed in Telleysniczky's fixative (70% ethanol containing 5% glacial acetic acid and 5% of 4% neutral buffered formaldehyde).

After 7 days of fixation tumors, which appear as pearly nodules on the surface of the lungs and urinary bladders, are counted under a dissecting microscope by two independent observers.

10 random samples of nodules are taken from the lungs and urinary bladders for histological evaluation and confirmation of adenoma. All tissues showing pathological changes are fixed in 4% buffered formaldehyde, embedded in paraffin and stained with H/E.

Data Analysis

Tumor incidences in different treatment groups are compared by the $\chi^2$-test. Food and water consumption in different treatment groups are compared by paired F- and t-test.

Results

Lung Tumors:

Peroral dosing of B(a)P and (NNK) once a week for 10 consecutive weeks result In a low number of lung tumors when the mice are terminated 12 weeks after the first treatment. FIG. 2 shows the number of lung tumors in each group. The tumors are small, approximately 0.5-1 mm in diameter.

Statistical analysis, using the $\chi^2$-test for comparison of the tumor incidence between groups, shows that chemopreventive feeding with Diet C (300 ppm acetylsalicylic acid, 0.02 µg/kg $1\alpha,25(OH)_2$-vitamin $D_3$ and 7500 ppm calcium significantly reduces tumor incidence when compared to the Group A, which received standard diet containing 5000 ppm calcium ($p<0.001$).

The mice group B which is fed on Diet B containing 2500 ppm calcium also has a lower tumor incidence than observed in Group A ($p<0.05$)

Urinary Bladder Tumors:

The number of urinary bladder tumors induced are lower than the number of lung tumors. The results are shown in FIG. 3.

Tumor incidence in urinary bladders also seem to be significantly reduced when comparing Group C on chemopreventive diet to Group A on standard diet ($\chi^2$-test, $p<0.025$). No significant reduction in tumor incidence is observed when low calcium Diet B is compared to Diet A.

Body Weights:

Body weights were measured weekly; starting in the week of first induction with carcinogen. No differences in body weights of the three groups are observed and the growth curves appears very similar. Thus, if body weights are taken as a measure of the general health condition of the mice there appears to be no difference between the groups.

Food and Water Consumption:

Food consumption is also measured weekly. There appears to be a tendency towards higher food consumption in Group C when compared to Group A. Drinking water intake appears to be similar between group.

Clinical Observations:

A few mice died in each group during the experiment. The cause of death was due to lesions caused by oral gavage.

From the results on body weights, food consumption and drinking water intake presented above it can be seen that the mice got into bad condition one week after dosing of carcinogens have started, but they gradually regained good condition during the rest of the study period.

During the study period a few incidences of mice with defined firm swellings in the axillary regions of the front legs and in the dorsal region of the neck were observed. No differences were observed between groups. The results shown that carcinogenic treatment induces subcutaneous transudates and cysts in the axillary regien of the front legs. Occationally hydrothorax is also observed.

CONCLUSION

Based on the results presented above it is concluded that chemopreventive feeding on a diet composed of 300 ppm acetylsalicylic acid, 0.02 µg/kg 1α,25(OH)$_2$-vitamin D$_3$ and 7500 ppm calcium in a highly significant manner reduces the incidence of lung tumors in mice, when compared to mice that were fed on a standard diet (p<0.001). This finding applies to both number of tumour-bearing animals and tumour multiplicity The same effect was observed on urinary bladder tumors, although at a less significant level (p<0.025) which was probably due to the low number of tumors found in the urinary bladders.

REFERENCES

Wargovich, M J. et al.: Calcium and vitamin D modulate mouse colon epithelial proliferation and growth characteristics of a human colon tumor cell line, Can J Physiol Pharmacol, 65,472-7, 1987.

Eisman, J A., et al.: Suppression of in vivo growth of human cancer solid xenografts by 1,25-dihydroxyvitamin D$_3$, Cancer Res, 47,21-5, 1987.

Hanif, A P., et al. NSAIDs inhibit the growth of colon cancer cell lines by a prostaglandin independent pathway, Gastroenterology, 108,A478, 1995.

Zhou, J. Y., et al.: Development of a novel 1,25 (OH)$_2$-vitamin D3 analog with potent ability to induce HL-60 cell differentiation without modulating calcium metabolism, Blood 78(1), 75-82, 1991.

Evans, S. R. et al.: 1,25-dihydroxyvitamin D3 synthetic analogs onhibit spontaneous metastases in a 1,2-dimethylhydrazine-induced colon carcigonesis model, Int J Oncol, 16(6), 1249-1254, 2000.

Kang, Y. et al.: TRansforming growth factor-β1 and its receptions in human lung cancer and mouse lung carcinogenesis, Experimental Lung Research, 26, 685-707, 2000.

Sunuga, N. et al.: Constitutive activiation of the Wnt signalling pathway by CTNNB I (β-Catanin) mutations in a subset of human lung adenocarcinoma, Genes, Chromosomes and Cancer, 30, 316-321, 2001.

Tsujiuchi, T. et al.: Mutations of adenomatous polyposis coli and β-catenin genes during progression of lung tumors induced by N-Nitrosobis (2-hydroxypropyl)amine in rats, Cancer Research, 60, 6611-6616, 2000.

Soslow, R A. et al.: COX-2 is expressed in human pulmonary, colonic, and mammary tumors, Cancer, 89, 2637-2645, 2000.

Yao, R. et al.: Inhibition of COX-2 and induction of apoptosis: two determinants of non-steroidal anti-inflammatory drugs' chemopreventive efficacies in mouse lung tumorigenesis, Exp. Lung Res, 26, 731-742, 2000.

Witschi, H.: Successful and not so successful chemoprevention of tobacco smoke-induced lung tumors, Exp Lung Res, 26, 743-755, 2000.

Rioux, N. et al.: Prevention of NNK-induced lung tumorgenesis in A/J mice by acetylsalicylic acid and NS-398, Cancer Res, 58, 5354-5360, 1998.

Duperron, C. et al.: Chemopreventive efficacies of aspirin and sulindac against lung tumorigenesis in A/J mice, Carcinogenesis, 18, 1001-1006, 1997.

Hong, W. K., Biological Effect and Tolerability of Celecoxib as a Chemopreventive Agent in Current and Former Smokers, published in IARC Cancer Databases on www.iarc.fr.

Cordon-Cardo, C. et al: Genetic and molecular markers of urothelial premalignancy and malignancy, Scand J Urol Nephrol, Suppl 205, 82-93, 2000.

Gonzalgo, M L. et al.: Biological pathways to bladder carcinogenesis, Sem Urol Oncology, 18, 256-263, 2000.

Wljkström, H. et al.: Prevention and treatment of urothelial premalignan and malignant lesions, Scand J Urol Nephrol, Suppl 205, 116-135, 2000.

Kbmhoff, M. et al.: Enhanced expression of cyclooxygenase-2 in high grade human transitional cell bladder carcinomas, Am J Pathol, 157, 29-35, 2000.

Castelao, J E et al.: Non-steriodal anti-inflammatory drugs and bladder cancer prevention, Br J Cancer, 82, 1364-1369, 2000.

Klan, R. et al.: Acetylsalicylic acid inhibition of n-butyl-(4-hydroxybutyl)nitrosamine-induced bladder carcinogenesis in rats, J Cancer Res Clin Oncol, 119, 482-485, 1993.

Rao, K V. et al.: Differential activity of aspirin, ketoprofen and sulindac as cancer chemopreventive agents in the mouse urinary bladder, Carcinogenesis, 17, 1435-1438, 1996.

Cohen, S M. et al.: Effect of aspirin on urinary bladder carcinogenesis initiated with N[4-(5-nitro-2-furyl)-2-thiazoiyl] formamide in rats, Cancer Res, 49, 372-377, 1989.

Konety, B R. et al: Effects of vitamin D (calcitriol) on transitional cell carcinoma of the bladder in vitro and in vivo, J Urol, 165, 253-258, 2001.

Prokopzyk, B. et al.: Chemoprevention of lung tumorgenesis induced by a mixture of benzo(a)pyrene and 4-(methylnitrosamino)-1-(3-pyridyl)-1-butanone by the organoselenium compound 1,4-phenylenebis(methylene)selenocyanate, Cancer Letters, 161, 35-46, 2000.

Pilegaard, K. et al.: Failure of the cultivated mushroom (Agaricus bisporus) to induce tumors in the A/J mouse lung tumor model, Cancer Letters, 120, 79-85-1997.

Hecht, S. et al.: Evaluation of butylated hydroxyanisole, myo-inositol, curcumin, esculetin, resveratrol and lycopene as inhibitors of benzo[a]pyrene plus 4-(mnethylnitrosamino)-1-(3-pyridyl)-1-butanone-induced lung tumorgenesis in A/J mouse, Cancer Letters, 137, 123-130, 1999.

Piyathilake, C J. et al.: Localized folate and vitamin B-12 deficiency in squamous cell lung cancer is associated with global DNA hypomethylation, Nutr Cancer, 37, 99-107, 2000.

Hirsch, F R. et al.: Early detection of lung cancer: clinical perspectives of recent advances in biology and radiology, Clin Cancer Res, 7, 5-22, 2001.

Saha, D. et al.: Synergistic induction of cyclooxygenase-2 by transforming growth factor-beta1 and epidermal growth factor inhibits apoptosis in epithelial cells, Neoplasia, 1, 508-517, 1999.

Kim, T. et al.: Alteration of cell growth and morphology by overexpression of transforming growth factor beta type factor II receptor in human lung adenocarcinoma cells, Lung cancer, 31, 181-191, 2002.

Marrogi, A J. et al.: Nitric oxide synthase, cyclooxygenase 2 and vascular endothelial growth factor in the angiogenesis of non-small cell lung carcinoma, Clin Cancer Res, 6, 4739-4744, 2000.

Hosomi, Y. et al.: Increased cyclooxygenase 2 (COX-2) expression occurs frequently in precursor lesions of human adenocarcinoma lung, Lung cancer, 30, 73-81, 2000.

Shirharama, T., Cyclooxygenase-2 expression is up-regulated in transitional cell carcinoma and its preneoplastic lesions in the human urinary bladder, Clin Cancer Res, 6, 2424-2430, 2000.

Ristimaki, A. et al.: Expression of cyclooxygenase-2 in human transitional cell carcinoma of the urinary bladder, Am J Pathol, 158, 849-853, 2001.

Rioux, N. et al.: The induction of cyclooxygenase-1 by a tobacco carcinogen in U937 human macrophages is correlated to the activiation of NF-kappaB, Carcinogenesis, 21, 1745-1751, 2000.

Witschi, H. et al.: Chemoprevention of tobacco-smoke lung carcinogenesis in mice after cessation of smoke exposure, Carcinogenesis, 21, 977-982, 2000.

Ehrich, E W. et al.: Clin. Pharmacol. Ther., 65, 336-347, 1999.

Johansson, S. et al.: Vitamin A antagonizes calcium response to vitamin D in man, J Bone Miner Res, 16, 1899-1905, 2001.

The invention claimed is:

1. A method for reducing the incidence of a lung cancer or a urinary bladder cancer that is inducible by benzo(a)pyrene or 4-(Methylnitrosamino)-1-(3-Pyridyl)-1-Butanone (NNK), in a human comprising administering to a human in need thereof an amount of a combination dosage, which comprises acetylsalicylic acid (ASA), 0.1 µg to 2 µg of 1,25 dihydroxy-cholecalciferol (1,25DHC), calcium and a pharmaceutically acceptable carrier, sufficient to reduce the incidence of a lung cancer or a urinary bladder cancer that is inducible by benzo(a)pyrene or NNK in said human.

2. The method according to claim 1, wherein the combination dosage comprises ASA in the range of 50 mg to 500 mg.

3. The method according to claim 1, wherein the combination dosage comprises calcium in the range of from 200 mg to 3000 mg.

4. The method according to claim 1, wherein the combination dosage comprises 50-75 mg of ASA, 500-1000 mg of calcium and 0.5-1 µg of 1,25 dihydroxy-cholecalciferol (1,25 DHC).

5. The method according to claim 1, wherein the combination dosage comprises 75 mg of ASA, 0.5 µg of 1,25 dihydroxy-cholecalciferol (1,25 DHC), and 500 mg of calcium.

6. The method according to claim 1, wherein the combination dosage comprises calcium in the range of from 200 mg to 3,500 mg.

7. The method according to claim 1, wherein the combination dosage comprises calcium in the range of from 250 mg to 3,000 mg.

8. The method according to claim 1, wherein the combination dosage comprises calcium in the range of from 300 mg to 2,500 mg.

9. The method according to claim 1, wherein the combination dosage comprises calcium in the range of from 400 mg to 2,000 mg.

10. The method according to claim 1, wherein the combination dosage comprises calcium in the range of from 500 mg to 1,000 mg.

11. The method according to claim 6, wherein the combination dosage comprises 50-500 mg of ASA.

12. The method according to claim 1, wherein the combination dosage comprises 25-400 mg of ASA.

13. The method according to claim 1, wherein the combination dosage comprises 50-300 mg of ASA.

14. The method according to claim 1, wherein the combination dosage comprises 75-150 mg of ASA.

15. The method according to claim 1, wherein the combination dosage comprises 75-100 mg of ASA.

16. The method according to claim 1, wherein the combination dosage comprises 50-500 mg of ASA.

17. The method according to claim 1, wherein the combination dosage comprises 1,25 dihydroxy-cholecalciferol (1,25 DHC) in the range of 0.2 µg to 1.5 µg.

18. The method according to claim 1, wherein the combination dosage comprises 1,25 dihydroxy-cholecalciferol (1,25 DHC) in the range of 0.3 µg to 1.0 µg.

19. The method according to claim 1, wherein the combination dosage comprises 1,25 dihydroxy-cholecalciferol (1,25 DHC) in the range of 0.4 µg to 0.75 µg.

20. The method of claim 1, further comprising examining said human for the presence of lung or bladder cancer.

21. A method for reducing the incidence of lung cancer or a urinary bladder cancer that is inducible by benzo(a)pyrene or 4-(Methylnitrosamino)-1-(3-Pyridyl)-1-Butanone (NNK) in a human comprising administering to a human in need thereof an amount of a combination dosage, which consists essentially of acetylsalicylic acid (ASA), 1,25 dihydroxy-cholecalciferol (1,25 DHC), calcium and a pharmaceutically acceptable carrier, sufficient to reduce the incidence of a lung cancer or a urinary bladder cancer that is inducible by benzo(a)pyrene or NNK in said human.

22. The method of claim 21, further comprising examining said human for the presence of lung or bladder cancer.

* * * * *